United States Patent
Lopez et al.

(12)

(10) Patent No.: US 6,514,698 B1
(45) Date of Patent: Feb. 4, 2003

(54) DNA METHYLTRANSFERASE GENOTYPING

(76) Inventors: Osvaldo J. Lopez, 1921 Pinedale Ave., Lincoln, NE (US) 68506; R. Michael Nelson, c/o Megabase Research Products, 2820 N. 48th St., Suite 110, Lincoln, NE (US) 68504

( * ) Notice: Subject to any disclaimer, the term of this patent is extended or adjusted under 35 U.S.C. 154(b) by 0 days.

(21) Appl. No.: 09/591,261

(22) Filed: Jun. 9, 2000

Related U.S. Application Data

(63) Continuation of application No. 09/143,696, filed on Aug. 28, 1998, now abandoned.
(60) Provisional application No. 60/057,068, filed on Aug. 29, 1997.

(51) Int. Cl.[7] .......................... C12Q 1/68; C12P 19/34; C07H 21/02; C07H 21/04
(52) U.S. Cl. ..................... 435/6; 435/91.2; 536/23.1; 536/24.3; 536/24.31; 536/24.33
(58) Field of Search .................. 435/6, 91.2; 536/23.1, 536/24.3, 24.31, 24.33

(56) References Cited

U.S. PATENT DOCUMENTS 5,455,166 A * 10/1995 Walker ...................... 435/91.2

FOREIGN PATENT DOCUMENTS

| WO | WO 90/05195 | 5/1990 | ............ C12Q/1/68 |
| WO | WO 90/12891 | 11/1990 | ............ C12Q/1/68 |
| WO | WO 92/20825 | 11/1992 | ............ C12Q/1/68 |
| WO | WO 95/25176 | 9/1995 | ............ C12Q/1/68 |
| WO | WO 96/27024 | 9/1996 | ............ C12Q/1/68 |

OTHER PUBLICATIONS

Matthews et al, "Analytical strategies for the use of DNA probes", Anal. Biochem. 169:1–25, 1988.*
Maeda et al, "A simple and rapid method for HLA–DP genotyping by digestion of PCR amplified DNA with allele specific restriction endonucleases", Human Immunology 27:111–121, 1990.*
Amersham Catalog, pp. 252–257, 1995.*
Achwal, C.W., "A sensitive immunochemical method for detecting 5mC in DNA fragments", FEBS Letters,(1982), vol. 150, No. 2, pp. 469–472.
Achwal, C.W., "Estimation of the amount of 5–methylcytosine in Drosophila melanogaster DNA by amplified ELISA and photoacoustic spectroscopy", IRL Press Limited, (1983) pp. 263–266.
Adams, R.L.P., "DNA Methylation. The Effect of Minor Bases on DNA–Protein Interactions", Biochem. J. (1990) 265:309–320.
Akimoto, K., "Luminol Chemiluminescence Reaction Catalyzed by a Microbial Peroxidase", Analytical Biochemistry, (1990) 189:182–185.
Annual Review of Genetics, (1991) vol. 25, Allan Campbell, Editor, Annual Reviews Inc., Palto Alto, CA.

Antequera, F., et al., "Unmethylated CpG islands associated with genes in higher plant DNA", The EMBO Journal, (1988) vol. 7, No. 8, pp. 2295–2299.
Appel, E., "Improved PCR Amplification/HhaI restriction for Unambiguous Determination of Apolipoprotein E Alleles", Clinical Chemistry (1995) vol. 41, No. 2, 187–190.
Barker, D., "Restriction Sites Containing CpG Show a Higher Frequency of Polymorphism in Human DNA", Cell (1984) vol. 36, 131–138.
Bickle, T.A., "The ATP–Dependent Restriction Endonucleases", Nucleases, edited by Stuart M. Linn, Richard J. Roberts, Cold Spring Harbor Laboratory, 1982, pp. 85–108.
Bird, A.P., "Use of Restriction Enzymes to Study Eukaryotic DNA Methylation: The Methylation Pattern in Ribosomal DNA from Xenopus Laevis", J. Mol. Biol. (1978) 118:27–47.
Brooks, D.A., "An improved method for the purification of IgG monoclonal antibodies from culture supernatants", Journal of Immunological Methods, (1992) 155:129–132.
Catalog, Chapter 1. In Situ Hybridization and Prins, Advanced Biotechnologies Literature, 1996, pp. 5–22.
Cinti, C., "Localization of Single Copy Gene by PRINS Technique", Nucleic Acids Research, (1993) vol. 21, No. 24 pp. 5799–5800.
Conrad, F., "A Solid Phase Method for Mapping Restriction Sites", Nucleic Acids Research (1992) vol. 20, No. 23 pp. 6423–6424.
Cox, D.W., "DNA Restriction Fragments Associated with $\alpha_1$–antitrypsin Indicate a Single Origin for Deficiency Allele PI Z", Nature, (1995) vol. 316, No. 4, 79–81.
Dorval, I., "Rapid Detection of 1078 delT Mutation by PCR–Mediated Site–Directed Mutagenesis: Detection of Cystic Fibrosis Carriers in a Celtic Population", Clinical Chemistry (1994) vol. 40, No. 12, 2318–2319.
Ehrlich, M., "5–Methylcytosine in Eukaryotic DNA", Science, (1981), 212:1350–1357.
Eichler, D.C., "Nucleotide–Specific Antibodies as Potential Blocking Agents in the Structural Analysis of Nucleic Acids" BBA (1974) 335:303–317.
Eiken, H.G., "Application of Natural and Amplification Created Restriction Sites for the Diagnosis of PKU Mutations", Nucleic Acids Research, (1991), vol. 19, No. 7, pp. 1427–1430.
Friedman, K.J., "Detecting Multiple Cystic Fibrosis Mutations by Polymerase Chain Reaction–Mediated Site–Directed Mutagenesis", Clinical Chemistry, (1991) vol. 37, No. 5, pp. 753–755.

(List continued on next page.)

Primary Examiner—Jeffrey Fredman
(74) Attorney, Agent, or Firm—McKee, Voorhees & Sease, P.L.C.

(57) ABSTRACT

DNA Methyltransferases can be utilized in methods for quickly and accurately: determining variations, mutations or polymorphisms in DNA sequences; identifying specific alleles in single copy genes; creating genomic fingerprints; creating DNA Paints; and generating ordered maps.

48 Claims, 14 Drawing Sheets

OTHER PUBLICATIONS

Haliassos, A., "Modification of Enzymatically Amplified DNA for the Detection of Point Mutations", (1989) *Nucleic Acids Research*, vol. 17, No. 9.

Halmann, M., "Rapid Identification and Quantitation of Small Numbers of Microorganisms by a Chemiluminescent Immunoreaction", *Applied and Environmental Microbiology*, (1977) vol. 34, No. 5, pp. 473–477.

Hawkes, R., "The Dot Immunobinding Assay", *Methods in Enzymology*, (1986) 121:484–491.

Hixson, J.E., "Restriction Isotyping of Human Apolipoprotein E by Gene Amplification and Cleavage with HhaI", *Journal of Lipid Research*, (1990) 31:545–548.

Humayun, M.Z., "Immunologic Studies on Nucleic Acids and Their Components I. an Analysis of the Specificity of Anti–Deoxyadenylate Antibodies by a Membrane–Binding Technique", *Biochimica et Biophysica Acta* (1973) 331:41–53.

Jarvis, E.E., et al., "DNA Nucleoside Composition and Methylation in Several Species of Microalgae", *J. Phycol*, (1992) 28:356–362.

Kemp, D.J., "Colorimetric Detection of Specific DNA Segments Amplified by Polymerase Chain Reactions", *Proc. Natl. Acad. Sci. USA*, (1989) vol. 86, pp. 2423–2427.

Khandjian, E.W., "Optimize Hybridization of DNA Blotted and Fixed to Nitrocellulose and Nylon Membranes", *Bio/Technology*, (1987), vol. 5.

Kricker, M.C., "Duplication–targeted DNA methylation and mutagenesis in the evolution of eukaryotic chromosomes", *Proc. Natl. Acad. Sci. USA*, (1992) 89:1075–1079.

Landgraf, A., "Direct Analysis of Polymerase Chain Reaction Products Using Enzyme–Linked Immunosorbent Assay Techniques", *Analytical Biochemistry*, (1991) 198:86–91.

Lautenberger, et al., "The DNA Sequence on Bacteriophage G4 Recognized by the *Escherichia coli* B Restriction Enzyme", *J. Mol. Biol.* (1979) 131:871–875.

Lautenberger, J.A., "Recognition site of *Escherichia coli* B Restriction Enzyme on φXsB1 and Simian Virus 40 DNAs: An Interrupted Sequence", *Proc. Natl. Acad. Sci. USA*, (1978) vol. 75, No. 5, pp. 2271–2275.

Lee, A.S., et al., "Location of the 5–Methylcytosine Group on the Bacteriophage φX174 Genome" *Journal of Virology*, (1974) 14:872–877.

Lubit, B.W., "Human Chromosome Structure as Revealed by an Immunoperoxidase Staining Procedure", *Exp. Cell Res.*, (1974) 89:426–428.

Miller, O.J., "Immunochemical Probes of Human Chromosome Organization", Pathobiology Annual, Harry L. Ioachim, M.D. Series Editor, Appleton–Century–Crofts/New York, publishers, vol. 5, 1975, pp. 71–103.

Montero, L.M., "The distribution of 5–methylcytosine in the nuclear genome of plants", *Nucleic Acids Research*, (1992), vol. 20, No. 12, pp. 3207–3210.

Munns, T.W., "Antibodies Specific for Modified Nucleosides: An Immunochemical Approach for the Isolation and Characterization of Nucleic Acids", *Progress in Nucleic Acid Research and Molecular Biology*, (1980), vol. 24, p. 133.

Nelson, M., "The Use of DNA Methylases to Alter the Apparent Recognition Specificities of Restriction Endonucleases", *Methods in Enzymology*, (1987) 155:41–46.

Nelson, M., "Use of DNA Methyltransferase/Endonuclease Enzyme Combinations for Megabase Mapping of Chromosomes", *Methods in Enzymology*, (1992) vol. 216, pp. 279–303.

Newton, C.R., "Analysis of any Point Mutation in DNA. The Amplification Refractory Mutation Systems (ARMS)", *Nucleic Acids Research*, (1989) vol. 17, No. 7.

Okamoto, et al., "Polymorphism of 5–Methylcytosine–Rich DNA in Human Acrocentric Chromosomes", *Human Genetics*, 1981) 58:255–259.

Okano, M., et al., "Cloning and characterization of a family of novel mammalian DNA (cytosine–5) methyltransferases", *Nature Genetics*, (1998) vol. 19:219–220.

Pintor–Toro, J.A., "Adenine Methylation in Zein Genes", *Biochem. and Biophys. Research Comm.*, (1987) vol. 147, No. 3, pp. 1082–1087.

Poupeye, E., "Synthesis of $^{11}$C–Labelled Thymidine for Tumor Visualization Using Positron Emission Tomography", *Appl. Radiat. Isot.* (1989) vol. 40, No. 1, pp. 57–61.

Reed, J.C., "A Strategy for Generating Monoclonal Antibodies Against Recombinant Baculovirus–Produced Proteins: Application to the Bcl–2 Oncoprotein", *Analytical Biochemistry*, (1992) 205:70–76).

Riordan, J.R., "Identification of the Cystic Fibrosis Gene: Cloning and Characterization of Complementary DNA", *Science* (1989) 245:1066–1073.

Roberts, R.J., "Rebase—Restriction Enzymes and Methylases", *Nucleic Acids Research*, (1996) vol. 24, No. 1, pp. 223–235.

Sano, H., "Deoxyribonucleic Acid Methyltransferase from the Eukaryote, *Chlamydomonas reinhardi*", *Eur. J. Biochem.* (1980) 105:471–480.

Sano, H., "Detection of heavy methylation in human repetitive DNA subsets by a monoclonal antibody against 5–methylcytosine", *Biochimica et Biophysica Acta.*, (1988) 951:157–165.

Sano, H., "Identification of 5–methylcytosine in DNA fragments immobilized on nitrocellulose paper", *Proc. Natl. Acad. Sci. USA*, (1980) vol. 77, No. 6, pp. 3581–3583.

Sawicki, D.L., "Immunochemical Detection of Minor Bases in Nucleic Acids", *Science* (1971) 174:70–71 (Abstract).

Stollar, B.D., "The Experimental Induction of Antibodies to Nucleic Acids", *Methods in Enzymology*, vol. 70, pp. 70–85.

Tagle, D.A., Characterization of Chromosomes and Localization of the rDNA Locus in the aye–aye (*Daubentonia madagascariensis*), *Cytogenet Cell Genet.* (1990) 54:43–46.

Trask, B.J., "Fluorescence in situ hybridization: Applications in Cytogenetics and Gene Mapping", *TIG* (1991), vol. 5, pp. 149–154.

Vaalburg, W., Amino Acids for the Measurement of Protein Synthesis In Vivo by PET, *Nucl. Med. Biol.*, (1992) vol. 19, No. 2, pp. 227–237.

van Ormondt, H., "Methylated Oligonucleotides Derived from Bacteriophage fd RF–DNA Modified In Vitro by *E. Coli* B Modification Methylase", *FEBS Letters*, (1973) vol. 33, No. 2.

Vilpo, J.A., "Radioimmunoassay of 5–Methyl–2'–Deoxycytidine. A Method for the Quantitation of DNA Methylation", *J. of Immunol. Methods*, (1984) 75:241–246.

Whithead, T.P., "Enhanced Luminescence Procedure for Sensitive Determination of Peroxidase–Labelled Conjugates in Immunoassay", *Nature,* (1983) 305:158–159.

Wigler, M., "The Somatic Replication of DNA Methylation, "0 *Cell,* (1981), vol. 24, 33–40.

Wigler, M.H., "The Inheritance of Methylation Pattern in Vertebrates", *Cell,* (1981), vol. 24: 285–286.

Wilcken, B., "Neonatal Screening for Cystic Fibrosis: A Comparison of Two Strategies for Case Detection in 1.2 Million Babies", *Journal of Pediatrics,* (1995) vol. 127, No. 6, pp. 965–970.

Wilson, G., "Restriction and Modification Systems", *Annu. Rev. Genet.* (1991) 25:585–627.

Yebra, M.J., "A Rapid and Sensitive Method to Measure DNA Endonuclease Activity" *Nucleic Acids Research* (1993) vol. 21, No. 24, pp. 5797–5798.

Matthews et al, "Analytical strategies for the use of DNA probes", Anal. Biochem. 169:1–25; 1988.

Maeda et al, "A simple and rapid method for HLA–DP genotyping by digestion of PCR amplified DNA with allele specific restriction endonucleases", Human Immunology 27:111–121:1990.

Amersham Catalog, pp. 252–257; 1995.

* cited by examiner

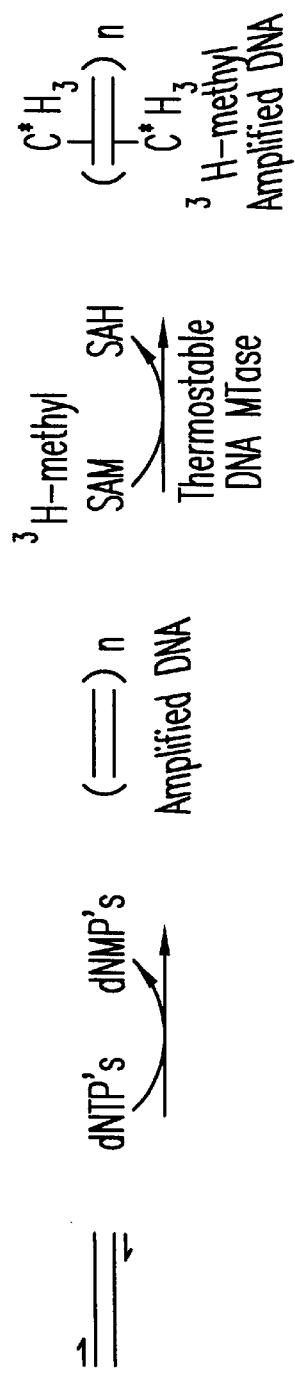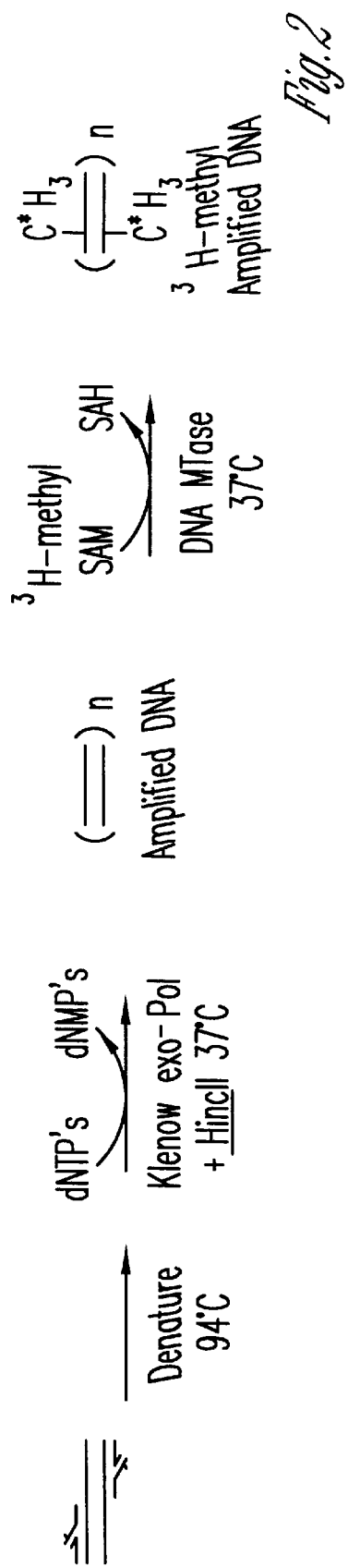

Yuk[a] GGTGGGAGAAGAAGATAAAAAG →
GGTGGGAGAAGAAGATAAAAAGTAACATCTTTCTGCCTTCCAGATGATTCGAAGA
ATTTCTCCATCCAAGTGCGGCAGGTGGAGGATTACCCTGTGGACATCTACTACTT
GATGGACCCTGTCTTACTCCATGCCCGGATGATCTGTGGAGCATCCAGAACCTGGGT

TGCA M.CviRI =Yuk[b]

ACCAAGCTGGCCACCCAGATGCGAAAGCTCACCAGTAACCTGCGGATTGGCTTCG
GGGCATTTGTGGACAAGCCTGTGTCACCATACATGTATATCTCCCACCAGAGGC
CCTCGAAAACCCCTGCTATGAGTAAGTCCCTCCCAGACGCCAGGACAGCATCC
TTTGCCCAGGAAGGTCCAAGTCCTGGTTCCTA
← CCAGGTTCAGGACCAAGGAT

Fig. 3A

TGC⁶mA M. CviRI = Yuk$^b$

5mCG M.SssI = Yuk$^a$ 22-mer primer
GAACCTGGGTACCAAGCTTGGC-->

GPIIIa DNA
GAACCTGGGTACCAAGCTTGGCCACCCAGATGCGAAGCTCACCAGTAACCTGCGGATTGGC
CTTGGACCCATGGTTCGAACCGGTGGGTCTACGCTTCGAGTGGTCATTGGACGCCTAACCG

<--GTGGTCATTGGACTCCTAACCG
22-mer primer

*Fig. 3B*

| | Complete Restriction Digestion | | | Partial Digestion |
|---|---|---|---|---|
| | Wild-type. | Heterozygote | Homozygote | Homozygote |
| Electrophoresis | a/a | a/b | b/b | b/b |
| M1 | ———— | ———— | ———— | ———— ← Partial digest band leads to misdiagnosis of homozygote DNA |
| M2 | ———— | ———— | ———— | ———— |
| M3 | ———— | ———— | ———— | ———— |

```
                                   m.MvaI    RsaI
HSV-1  CCAAGCTGACGGAGACATCTACAAGGTCCCCCTGGACGGGTACGGGCCGCATG
       ||||||||||||||| ||||||||||||||| |||| |||||| ||||||||
HSV-2  CCAAGCTGACGGAGATCTACAAGGTCCCGCTCGACGGGTACGGGCGCATG
                                    m.TaqI RsaI  HhaI m.MspI     BstUI
HSV-1  AACGGCCCGGGGGCGTGTTTCGCGTGTGGGACATAGGCCAGAGCCACTTCCAGAA
       |||||||||||| ||||||| ||||||||||||| ||||||||||||||||||||
HSV-2  AACGGCCCGGGGTGTGTTCCGCGTGTGGGACATCGGCCAGAGCCACTTCCAGAA
                 m.MspI     BstUI
```

Fig. 5

DNA METHYLTRANSFERASE GENOTYPING

CROSS-REFERENCE TO RELATED APPLICATIONS

Applicants claim the benefit of the earlier filed co-pending prior application Ser. No. 09/143,696 filed Aug. 8, 1998 which was a continuation of provisional No. 60/057,068, filed Aug. 29, 1997.

GRANT REFERENCE

Work for this invention was funded at least in part by a grant from United States Department of Agriculture, Small Business Innovation Research Program, Grant Proposal No. 97-03376; and United States National Institutes of Health, Grant No. 1-R43-GM56595-01/120PW. The Government may have certain rights in this invention.

FIELD OF THE INVENTION

This invention relates to methods for DNA genotyping and gene mapping whereby nucleotide variations, mutations and polymorphisms are quickly and accurately detected by the enzymatic methylation of DNA using sequence-specific DNA methyltransferases. In particular, a novel method is described in which DNA can be "painted" at specific sites using radiometric or immunochemical detection. This novel methodology has been identified by the term "DNA Paint". DNA methyltransferases can be used alone, or in combination with restriction endonucleases, to (a) diagnose diseases of plants, animals, or humans; (b) map genes; or (c) detect genetic mutations or polymorphisms.

BACKGROUND OF THE INVENTION

Starting in the early 1970's with the emergence of the recombinant DNA methods and rapid DNA sequence technologies that followed soon thereafter, scientists have relied upon restriction endonucleases to study the genetic makeup of plants and animals. The medical field has shown great advancements through the use of this molecular genetic revolution through the identification of nucleic acid variations, mutations, and polymorphisms within genes and over entire genomes. In addition, the ability to identify and recombine specific alleles for genes of interest allow researchers to create improved livestock or plant varieties much more quickly than traditional breeding methods have allowed.

The discovery of sequence-specific DNA cutting enzymes, restriction endonucleases, made the development of recombinant DNA technologies possible. Over 2,000 different sequence-specific endonucleases have been characterized, of which about 200 are available. R. J. Roberts & D. Macelis, "REBASE—Restriction enzymes and methylases", *Nusleic Acids Res.*, 24:223–235 (1996), incorporated herein by reference. These restriction endonucleases have been widely used in RFLP mapping, DNA fingerprinting, gene mapping, to detect mutations responsible for heritable human diseases and polymorphisms associated with traits of interest in animal and plant breeding programs, and to diagnose infectious disease agents or viral, bacterial, or fungal origin.

Gene mapping, DNA fingerprinting, and RFLP technologies routinely exploit the variations and mutations between the genomes of different individuals or species or varietal populations. When a point mutation, insertion, or deletion, alters the DNA sequence within a genome, the restriction endonuclease enzyme can detect these changes in nucleic acid sequence if the change creates or destroys a restriction endonuclease recognition sequence. Restriction endonucleases are sequence-specific DNA-cutting enzymes which recognize a specific nucleic acid sequence pattern and cleave DNA strands at specific locations. The restriction enzymes most often used in gene mapping and DNA fingerprinting technologies are Type II bacterial restriction enzymes, most of which recognize 4 to 6 base pair recognition sequences. Therefore, on average, most DNA restriction fragments are $4^4$ to $4^6$ (256 to 4096) base pairs (bp) long. When a mutation or variation occurs within one of these DNA sequence recognition sites, those restriction enzymes which cleave at that recognition sequence will no longer be able to cut at that site if the site is destroyed. Conversely, if a DNA sequence recognition site is created, the restriction enzyme for that site will be able to cleave the DNA where it could not previously. It is this variation in the presence and absence of restriction enzyme recognition sites within the genomes of different individuals that allows for DNA mapping and genetic fingerprinting using restriction enzymes. (Botstein et al., "Construction of a genetic linkage map in man using restriction fragment length polymorphisms", *Am. J. Human Genetics*, 32:314–331 (1980); R. White and J. J. Lalouel, "Chromosome Mapping with DNA Markers", *Scientific American*, 258:40–48 (1988).

While the advent of the restriction enzymes has revolutionized molecular genetics, it has not come without its inherent weaknesses. In order to visualize the changes in restriction endonuclease target sites (and to therefore define a restriction isotype or an allelic fingerprint), the DNA fragments that result from restriction endonuclease cleavage must be separated by size. In short, if DNA is cut into pieces then the resulting pieces must be separated. Differences in fragment size create different morphological patterns, hence polymorphisms, for each individual or trait of interest. These polymorphic patterns (DNA fingerprints) are best observed when run out by electrophoresis on agarose or polyacrylamide gels.

Another limitation using bacterial restriction enzymes in RFLP mapping or genotyping is that most mutations or polymorphic sites in DNA do not occur within these relatively rare (4 to 6 bp) endonuclease recognition sequences. The present invention overcomes this limitation through the use of sequence-specific DNA Methyltransferases (MTases) which can recognize short 2 to 4 bp sequence recognition sites as well as longer 4 to 8 bp sequence recognition sites. In particular, 75% of point mutations responsible for all known heritable human diseases occur at CG sites. D. Cooper & H. Youssoufin, "The CpG dinucleotide and human genetic disease", *Human Genetics* 78:151–165 (1988), incorporated herein by reference. Several DNA MTases recognize 2 bp CG sites, such as M.SspMQI, M.SssI, and M.DmtI of mouse (Okano, M., et al, "Cloning and Characterization of a Family of Novel Mammalian DNA (Cytosine-5) Methyltransferases", *Nature Genetics*, Vol. 19, Jul. 1998, 219–220), human, Arabidopsis, and algal virus DNA MTases (Nelson et al., "DNA Methyltransferases and Site-specific Endonucleases Encoded by Chlorella Viruses", in: G. P. Jost & H. P. Salusz HP, eds., DNA Methylation, Birkauser & Basel, pp. 186–211 (1993)). In contrast, no known restriction endonucleases recognize CG or any other dinucleotide sequences.

The present invention uses DNA MTases rather than restriction enzymes to overcome many of the above-mentioned problems. Each restriction endonuclease has a companion sequence-specific DNA methyltransferase (MTase) which has the same DNA recognition site. W. Arber & S. Linn, "DNA Modification and Restriction", *Ann. Rev. Biochem.* 38:467–500 (1969), incorporated herein by reference. Several hundred of these DNA MTase specificities are known (McClelland et al., "Effect of site-specific modification on restriction endonucleases and DNA MTases", *Nucleic Acids Res.* 22:3640–3659 (1994), incorporated herein by reference) and more are being discovered each year. In addition, as mentioned above, there are several DNA MTases which recognize 2 to 4 bp DNA sequences, such as the CG dinucleotide sequence, whereas there are no known restriction endonucleases with such short recognition sequences. As described in this patent application for the first time, it is possible to use methyltransferases rather than restriction enzymes to detect genetic polymorphisms and mutations at 2 to 8 bp sites within genomic DNA.

The present invention can utilize PCR amplification and sequence-specific DNA methylation to detect the presence or absence of specific DNA methyltransferase recognition sites.

DNA methyltransferases (MTases) catalyze the transfer of methyl groups from S-Adenosylmethionine (SAM) to specific sites in double-stranded DNA, yielding methylated DNA and S-Adenosylhomocysteine (SAH).

$$\text{DNA} + \text{SAM} \xrightarrow{\text{DNA MTase}} \text{methyl-DNA} + \text{SAH}$$

If radioactive $^3$H-methyl-SAM is used as a substrate, then the number of methyl groups incorporated into DNA can be measured by trichloroacetic acid (TCA) precipitation of $^3$H-methyl-DNA, followed by liquid scintillation counting.

$$\text{DNA} + {}^3\text{H-methyl-SAM} \xrightarrow{\text{DNA MTase}} {}^3\text{H-methyl-DNA} + \text{SAH}$$

This reaction is usually termed a "SAM-dependent DNA methyltransferase reaction". However, it might be better termed a "DNA-dependent SAM methyl transfer reaction", since the $^3$H-methyl groups are incorporated into DNA only if a sequence-specific MTase recognition site is present. If one or more DNA MTase sequence recognition sites are present, then the number of such sites can be measured quantitatively based on a linear increase in tritium counts per minute (cpm) of radiolabeled $^3$H-methyl DNA.

Sequence-specific DNA MTase enzymes have been used only sparingly in megabase mapping experiments. M. Nelson & M. McClelland, "The use of DNA MTase/Endonuclease enzyme combinations for megabase mapping of chromosomes by pulsed field gel electrophoresis", *Methods in Enzymolog* 216:279–303 (1992), incorporated herein by reference. These megabase mapping experiments utilize sequential multi-step DNA methylation and restriction enzyme cleavage reactions to create chromosome fragments in the size range from 50 to 2000 kilobases (kb) that are subsequently analyzed using pulse field gel electrophoresis (PFGE). See D. C. Schwartz & C. R. Cantor, 37 *Cell* 67 (1984); Gardiner et al., 12 *Somatic Cell. Mol. Genet.* 185 (1986); Cantor et al., 17 *Ann. Rev. Biophys. Chem.* 287 (1988). These experiments describe how MTases can be used to increase the apparent specificity of restriction enzymes. However, they do not describe how MTases can be used to "paint" DNA at specific 2 to 8 bp sites using either radioactive ($^3$H-methyl-DNA) or immunochemical detection. Furthermore, the techniques of the above cited references are normally carried out in situ on unsheared chromosomes embedded in agarose plugs and it has proven necessary to require: (1) that the purity of the MTases and the restriction endonucleases be critically controlled, (2) that the number of steps be kept at a minimum, and (3) that the reaction conditions be defined which are compatible with PFGE separation. This technique includes the inherent drawbacks of PFGE such as the time and effort required to prepare high molecular weight substrates and to run pulsed-field gels. The present invention overcomes these problems by creating smaller fragments of genomic DNA or utilizing PCR-type techniques, thus eliminating the need for agarose embedded in situ reactions or completely eliminating the need for electrophoresis. Further, the present invention allows for much finer mapping—down to the nucleotide level—and exploitation of this information for such uses as diagnostic testing in clinical settings.

In general, DNA MTases have been used neither to map genes nor to detect mutant alleles. The present invention shows how DNA MTases can be used to radio- or immunochemically "paint" DNA in order to identify polymorphic sites or mutations. Using DNA MTases, one can determine genotypes with significant improvements in speed, accuracy and specificity over RFLP mapping and other methods utilizing restriction endonucleases. In short, the methods of the present DNA MTase invention are extremely fast, do not require gel electrophoresis or nucleic acid hybridization, and result in simple quantitative and/or qualitative assays. As a result, DNA MTase genotyping of the present invention lends itself to automation. Rapid automated PCR-based MTase genotyping may be especially useful in high throughput diagnostic laboratories or in situations where fast, easy, reproducible results are required, such as clinical laboratory or hospital settings.

The present invention does not require that DNA fragments be separated on agarose gels. Southern transfers, nucleic acid hybridization or radioactive labeling are not required, although these are possible uses of DNA MTases in certain embodiments of the present invention. Most importantly, since MTases do not cut the sugar-phosphate backbone of DNA, there are no DNA fragments that need to be separated. The present invention overcomes the lengthy and laborious dependence on gels and Southern transfers. The present invention allows for quick and quantitative analysis without the need to separate by fragment size using gels or time-consuming Southern transfer techniques. Certain embodiments of the present invention do not require the use of restriction enzymes at all. This independence from endonucleases allows the diagnostician or researcher to avoid erroneous results due to incomplete restriction enzyme digestions. The present invention also allows for the use of very short PCR products (30–100 bp). Since the PCR reaction cycle times are shortened to a few seconds, the concentrations of amplified DNA are increased, resulting in improved signal-to-noise. Thus the present inventive methods utilizing DNA MTases for genotyping are faster, more accurate, and easier to perform than the methods known to those skilled in the art utilizing bacterial restriction enzymes.

It is an object of the present invention to provide a method of genotyping DNA utilizing a DNA methyltransferase in conjunction with a PCR amplicon so that a quick and accurate determination of a mutation or nucleic acid variation can be determined.

A second object of the invention is to provide a method utilizing a DNA methyltransferase to genotype DNA whereby the method of detection relies on immunochemical (non-radioactive) detection, so that radioactive label is not required.

A third object of the invention is to provide a method of genotyping DNA utilizing a DNA methyltransferase without the need for agarose gel fractionation of DNA or Southern transfer.

A fourth object of the invention is to provide a method of ordered genetic maps of PCR-amplified DNA utilizing biotinylated primers and combinations of DNA methyltransferases and endonucleases. In other words, not only can the presence of MTase sites be determined, but their positions relative to the 5' biotinylated end can be located.

A fifth object of the invention is to provide a method of DNA genotyping utilizing DNA methyltransferases whereby the determination of mutation or variation can be accomplished in a single-container reaction with no need for removal of reaction precursors, thus allowing for an even faster turnaround time.

A sixth objective of the invention is to provide a method utilizing DNA methyltransferases to identify individual alleles associated with disease traits or traits of economic importance and which could further be automated for fast, accurate and economic results.

A seventh objective is to provide a genotyping method which relies upon detecting the presence or absence of DNA MTase recognition sites, so that detection of specific DNA regions or alleles can be automated.

Additional objects and advantages of the invention will be set forth in part in the description that follows, and in part will be obvious from the description, or may be learned by the practice of the invention. The objects and advantages of the invention will be obtained by means of the instrumentalities and combinations, particularly pointed out in the appended claims.

SUMMARY OF THE INVENTION

To achieve the objects and in accordance with the purpose of the invention, as embodied and broadly described herein, the present invention provides a method for exploiting DNA MTases, ability to methylate DNA at specific nucleic acid sequences. The sequence-specific DNA MTases can be used to detect the presence of specific recognition sites in nucleic acid molecules. Known or unknown sequences can be genotyped using DNA MTases. For example, MTases can be used to detect genetic mutations or polymorphisms or simply to gain DNA sequence information of unknown genes. The ability, or inability, of these DNA MTases to methylate at the sites of mutation or polymorphism are then detected by means which can include immunochemical or radiometric detection methods. Upon detection of the sites of methylation, DNA sequence information can be compiled, analyzed and referenced.

Numerous immunochemical detection methods are known to those of ordinary skill in the art and are readily available through commercial sources such as Fisher Scientific, Pittsburgh, Pa.; Boehringher Mannheim Corp., Indianapolis, Ind.; and Vector Laboratories, Burlingame, Calif. These immunodetection methods rely upon haptens such as biotin, digoxigenin, or those detected by antibodies or lectins conjugated with enzymes such as alkaline phosphatase, horseradish peroxidase, or β-Galactosidase. See, Christopher Kessler, "The digoxigenin:anti-digoxigenin (DIG) technology—a survey on the concept and realization of a novel bioanlytial indicator system", *Molecular and Cellular Probes*, 5:161–205 (1991). Immunochemical detection methods can include, among others, labeling systems which utilize chemiluminescence substrates, chromogenic substrates, rhodamine, and fluorochrome-labels such as fluorescein isothiocyanate and tetramethylrhodamine. Numerous radiometric detection methods are also known to those of ordinary skill in the art and readily available through commercial sources such as Amersham Lifesciences, Arlington Heights, Ill. and New England Nuclear, Boston, Mass. However, the use of sequence-specific DNA MTases in vitro, followed by immunochemical detection of methylated DNA has not been previously described. Furthermore, none of these earlier methods allow DNA to be internally labeled at defined 2 to 8 bp sites.

The methods of this invention include as preferred embodiments in which these DNA MTases are utilized: (1). a radiometric $^3$H-methyl incorporation assay, theoretically also $^3$H$_3$C$^{11}$-, position-labeled methyl assay; (2) a non-radioactive immunochemical detection; (3) a combination of sequence-specific DNA methylation, restriction enzyme digestion, and Southern blotting ("DNA Paint"); and (4) an anchored PCR format in which biotinylated primers are used in combination with DNA MTases and endonucleases. Importantly, this last format allows ordered maps to be rapidly constructed without the need for either electrophoresis or nucleic acid hybridization.

In one embodiment, the invention comprises a method for genotyping an unmethylated DNA fragment produced by PCR amplification. Using PCR primers that flank the region of interest, enough DNA is amplified to conduct a series of sequence-specific DNA MTase and/or restriction endonuclease reactions. The design of PCR primers is known to those of skill in the art and are described in Mullis et al., *The Polymeragg Chain Reaction*, Burkhauser Publishers, Boston, Mass. (1994), the disclosure of which is incorporated by reference. Amplified DNA is treated with selected DNA methyltransferases and radioactively-labeled-methyl-SAM. The radioactively labeled methyl group will thus be incorporated into a specific 2 to 8 bp site in the DNA. If appropriate, sufficient DNA may be put into reaction tubes to allow for digestion by selected restriction enzymes. The amount of radioactively labeled methyl DNA will be measured using radiometric assay methods well known to those of ordinary skill in the art. This technique will identify a DNA MTase genotype for each recognition sequence site within the PCR generated DNA fragment.

In a second embodiment of the invention, the genotyping of genes, or alleles of genes, associated with a disease condition, or a trait of economic interest in livestock or plants, can be determined utilizing DNA methyltransferases. DNA is first amplified using PCR primers that flank the gene, or segment of the genome, of interest. The amplified DNA is methylated with a radioactively labeled methyl group at a specific site known to vary from one allele to another. A sequence-specific DNA MTase can then be used to detect a defined genetic variation or mutation. Methylation of the DNA may be accomplished either at the same time as the amplification of the PCR fragment using thermostable MTases or following the amplification of the PCR fragment of interest if no thermostable methyltransferase is available for the site of interest. The presence or absence of the variation or mutation in question is determined by radiometric assay. If adequate signal-to-noise is achieved, then the wild type (a/a) state, heterozygous (a/b) state, or homozygous (b/b) state can be detected for that site.

In a third embodiment, the presence or absence (and the quantification of multiple sites) can be determined utilizing immunochemical detection rather than radioactive detection of methylated DNA. Detection of methylated DNA can be accomplished utilizing the above methods or other methods, as will be evident from this disclosure, by enzymatically incorporating non-radioactive methyl groups utilizing DNA methyltransferase. The resulting DNA can be spotted on to a fixed surface such as nitrocellulose or nylon membranes and adhered through routine methods known in the art. The DNA can also be separated by size on an agarose gel and transferred onto membranes using the Southern transfer technique. The membranes can then blocked to prevent background signal due to non-specific noise. In one example of this embodiment, a nylon membrane containing methylated DNA fragments are UV-irradiated and then incubated in the presence of anti-$^{6-}$smethyladenine rabbit immune serum in buffered nonfat milk blocking solution. The filters are washed and treated with a solution containing alkaline-phosphatase conjugated goat anti-rabbit IgG or antiserum. After washing, NBT/NCIP substrate for alkaline-phosphatase is added. Methylated $^{6m}$A DNA is detected as blue spots or bands on a white nylon filter background.

In a fourth embodiment (sequence-specific "DNA Paint" Format), a combination of sequence-specific DNA methylation, restriction digestion, and Southern blotting technique allows methylated DNA fragments to be selectively stained. Such "methylase painting" of DNA fragments can be accomplished by digesting DNA with restriction endonucleases, and methylating the resultant DNA fragments with DNA methylases that have a different sequence specificity site. In general, DNA methylation is conducted prior to endonuclease digestion. However, the order can usually be reversed. The resultant fragments are then separated by size utilizing an agarose gel. After electrophoresis, the DNA is transferred from the gel to a membrane (nylon or nitrocellulose) using Southern transfer technique or other transfer methods known to those of ordinary skill in the art. The membrane-bound methylated fragment patterns are detected using radiometric techniques (if radioactively-labeled-methyl groups were incorporated) or immunochemical detection methods. This embodiment results in a DNA membrane or image exhibiting a unique pattern, or "DNA Painting", for each genome or DNA fragment of interest. Simply put in binary code, any particular DNA fragment is either radioactively or immunochemically labeled (1) or else it is not labeled (0). The presence or absence of methylated 2 to 8 bp DNA MTase recognition sites appear as colored bands or spots.

In a fifth embodiment, the invention comprises a method whereby the PCR fragment is anchored to a solid matrix, for example, a magnetic bead or Streptavidin SPA bead, so that radioactively labeled methyl groups can be counted using appropriate radiometric assays.

BRIEF DESCRIPTION OF THE DRAWINGS

FIG. 1 shows a graphic representation of a single reaction mixture for thermocycling wherein DNA is amplified using polymerase chain reaction (PCR) and simultaneously methylation is carried out using a thermostable DNA methyltransferase.

FIG. 2 shows a graphic representation of a single reaction mixture for thermocycling wherein DNA is amplified using strand displacement amplification and methylated using DNA methyltransferase, simultaneously.

FIGS. 3A and 3B are double-stranded DNA sequences from the human platelet antigen glycoprotein (GPIIIa) gene. FIG. 3A shows the 362 bp fragment (SEQ ID NO: 1) containing the mutated M.CviRI recognition sequence. FIG. 3B shows the 61bp fragment (SEQ ID NO: 2) containing both the wild type M.SssI recognition sequence and the mutated CviRI sequence. Primers used on opposite sides of the GPIIIa CG to CA mutation are also indicated as shown (SEQ ID NOS: 3 and 4).

FIG. 5 is a diagram showing the actual sequence of two alleles, one from HSV-1, (SEQ ID NO: 5) and the other from HSV-2(SEQ ID NO: 6). This sequence shows how it is possible to PCR amplify and map an amplicon using a combination of MTases and restriction enzymes.

FIG. 7A is a photograph of an ethidium bromide stained agarose gel showing lambda dam$^+$ and dam$^-$ phage DNA. The lambda dam-DNA is naturally methyl-deficient (negative control; lanes 5–8), and the lambda dam$^+$ DNA is naturally methylated (lanes 1–4). Lanes 2 and 6 are digested with EcoRI, lanes 3 and 7 are digested with BamHI, and lanes 4 and 8 are digested with HindIII.

FIG. 7B is a photograph of, the same gel after transfer of DNA to a nylon membrane. DNA is painted purple after immunochemical detection using rabbit anti-$^{6m}$A-antibodies and alkaline phosphatase-conjugated goat-anti-rabbit IgG. Methylated DNA fragments appear as dark purple/black bands on a light purple background. As shown in lanes 2, 3 and 4, only those bands containing $^{6m}$A-methylated G $^{6m}$ATC sites are immunostained. This figure shows that methylated DNA fragments can be detected after electrophoresis and transfer to a nylon filter. Only those fragments with at least 6 to 8 $^{6m}$A sites can be detected. Improved sensitivity was subsequently achieved, as shown in FIGS. 9 to 12.

FIG. 8A is a photograph of the ethidium bromide stained gel and FIG. 8B is a photograph of the anti $^{6m}$A immunophosphatase stained nylon membrane that corresponds to the gel in FIG. 8A.

FIG. 9A is a photograph of an ethidium bromide stained agarose gel containing phage T7 DNA. The unmethylated T7 DNA (negative control), G$^{6m}$ATC-methylated DNA (T7 M.dam) and TCG$^{6m}$A-methylated DNA (T7 M.Taq I) were digested using DpnII, TaqI, SpeI or NruI endonucleases (lanes A–L, respectively).

FIG. 9B is a photograph of a nylon membrane following transfer of the gel in FIG. 9A. FIG. 9B further shows the immunochemical detection of the $^{6m}$A methylated DNA. This figure shows that an in vitro sequence-specifically methylated DNA fragment can be detected after electrophoresis and transfer to a nylon filter.

FIG. 10A is a photograph of an ethidium-bromide stained agarose gel showing a 536 bp amplicon from human β-globin gene. The amplicon was digested with Nco I (C↓CATGG; lanes 2 and 6), Ava II (G↓GWCC; lanes 3 and 7), or Dpn II (↓GATC; lanes 4 and 8).

FIG. 10B is a photograph of an anti-$^{6m}$A immunostained nylon membrane following transfer of the gel is shown in FIG. 10A. The amplicon was not methylated (lanes 1–4), or else methylated at G$^{6m}$ATC sites using M.dam MTase (lanes 5–8). FIG. 10B shows sequence-specific immunophosphatase/BCIP immunochemical detection of DNA fragments containing G$^{6m}$ATC sites.

FIG. 10C is a map of the human β-globin 536 bp amplicon showing the expected sizes of methylated DNA fragments.

FIG. 11A is a photograph of an ethidium-bromide stained agarose gel showing a 1850 bp amplicon from human β-globin gene. The amplicon was digested with EcoRI (G↓AATTC; lanes 3 and 7), BsrGI (T↓GTACA; lanes 4 and 8), BamHI (G↓GATCC; lanes 5 and 9).

FIG. 11B is a photograph of a $^{6m}$A-methylated DNA fixed to a nylon membrane following transfer of the gel in FIG. 11A. The amplicon was not methylated (lanes 2–5) or else methylated in vitro by M.EcoRI MTase (GA$^{6m}$ATTC; lanes 6–9). FIG. 11B further shows the sensitivity of immunochemical detection of the GA$^{6m}$ATTC-methylated DNA using rabbit anti$^{6m}$A antibodies followed by alkaline-phosphatase conjugated goat anti-rabbit antibodies and fast red substrate (Pierce, Rockford, Ill.).

FIG. 11C is a map of the 1.85 Kb 9-globin amplicon.

FIG. 12A is a photograph of an ethidium-bromide stained agarose gel showing a 536 bp amplicon from human β-globin gene. The amplicon was methylated with M.HaeIII MTase (GGC$^{5m}$C; lanes 6–8), M.dam MTase (G$^{6m}$ATC; lanes 9–11), M.MvaI MTase (C$^{4m}$CWGG; lanes 12–14), or not methylated (lanes 1–5). The amplicon was digested with NcoI (C↓CATGG; lanes 2, 7, 10 and 13), DpnII (↓GATC; lanes 3 and 11), BstNI (CC↓WGG; lanes 4 and 14), HaeIII (GG↓CC; lanes 5 and 8). Note that amplicons in lanes 4, 8 and 11 are not digested because cleavage by BstNI, HaeIII, and DpnII is blocked by MTases, M.MvaI, M.HaeIII and M.dam, respectively.

FIG. 12B further shows the immunochemical detection of the $^{6m}$A methylated DNA using rabbit anti$^{6m}$A antibody followed by alkaline-phosphatase anti-rabbit secondary antibody and fast red substrate (Pierce, Rockford, Ill.).

FIG. 12C is a map of the β-globin 536 bp amplicon showing the expected sizes of methylated DNA fragments.

DETAILED DESCRIPTION OF THE INVENTION

Figures 4A, 4B:
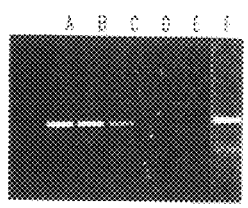
FIG. 4A is a graphic representation of a partial digest band of homozygous Yuk$^{b/b}$ compared to complete restriction digestion of wild type, heterozygous or homozygous Yuk alleles.
FIG. 4B is a photographic representation of an agarose gel containing a partial digest of Yuk$^{b/b}$ compared to Yuk$^{a/a}$ Yuk$^{a/b}$ and Yuk$^{b/b}$ fragments generated by the PCR amplified DNA MTase genotype method. The far left lane is uncut DNA, the next lanes are genotype a/a, a/b, and b/b. The far right lane represents a partial b/b digestion that could be mistaken for an a/b genotype.

Reference will now be made in detail to the presently referred embodiments of the invention, which together with the following examples, serve to explain the principles of the invention.

The DNA of bacteria that encode type II restriction endonucleases are protected from endonuclease catalyzed auto degradation by corresponding isospecific methylases. Specific DNA methyltransferases ". . . recognize the same nucleotide sequences as their cognate endonucleases and transfer a methyl group from S-adenosyl methionine to specific adenine (forming N$^6$-methyladenine) or cytosine (forming 5-methylcytosine) residues within the site." Maxine Singer and Paul Berg, *Genes and Genomes* 253 (University Science Books 1991). As a result, the restriction endonuclease cannot cleave at that modified (methylated) recognition site. In addition, many bacterial species contain enzymes, the dam and dcm methylases, which do not have a cognate restriction endonuclease and yet will methylate DNA at well-defined recognition sequences. Roger L. P. Adams, "Review Article: DNA Methylation—The Effect of Minor Bases on DNA-Protein Interactions", 265 *Biochem. J.* 309, 309–10 (1990). As new DNA methyltransferase genes are isolated and sequenced, predicted amino acid sequences specific to each type of methylase are identified as conserved regions. Id.

DNA methyltransferases are available through commercial suppliers such as New England Biolabs, Beverly, Mass.; MBI Fermentas, Flamborough, ON, Canada; and Megabase Research Products, Lincoln, Nebr. In addition, the Type II DNA methylases (S-Adenosylmethionine: DNA Methyltransferases) have been purified from a number of different sources and purification procedures have been published and are therefore well known to those of ordinary skill in the art. See Michael Nelson and Michael McClelland, "Purification and Assay of Type II DNA Methylases", 155 *Methods in Enzymology* 332, 332–341 (1987). Extensive lists of known DNA methyltransferases have been published such as that in Table III of M. McClelland et al., "Effect of Site-Specific Modification on Restriction Endonucleases and DNA MTases", 22 *Nucleic Acids Research* 3640–3659 (1994). Bee also R. J. Roberts and D. Macelis, "REBASE—Restriction Enzymes and Methylases", 22 *Nucleic Acids Research* 3626–3639 (1994); Michael Nelson et al., "DNA Methyltransferases and DNA Site-Specific Endonucleases Encoded by Chlorella Viruses", (Jost, J. P., and Sulsz H. P., eds., DMA Methylation, Birkauser, Basel) 186–211 (1993); and Geoffrey G. Wilson & Noreen E. Murray, "Restriction and Modification Systems", 25 *Anne Rev. Genetics* 585–627 (1992).

DNA methyltransferases can be selected for use in the present invention based on known sequences of regions of DNA from genes or intergenic regions of interest. DNA methyltransferases can also be selected randomly, in much the same way that restriction endonucleases are randomly chosen for mapping and genotyping experiments. When determining the genotype of a specific region of DNA or gene of interest, a DNA methyltransferase is chosen that will methylate a specific recognition sequence site within that DNA sequence. If the sequence is not known, then the restriction endonucleases (R) and their cognate DNA methylases (M) can be utilized to determine both the presence or absence of their respective R or M recognition sites and the order in which they occur. These and other embodiments will be more fully detailed in the disclosure that follows.

The present invention relates to the use of DNA MTasesto detect genetic mutations or polymorphisms at specific DNA sites. A single nucleotide point mutation or polymorphism can create or destroy the sequence-specific recognition site of a DNA MTase and its companion restriction endonuclease. The ability of a DNA MTase to methylate at the site of a mutation or polymorphism is detected by means which ran include immunochemical detection or radiometric detection methods. Once the sites of DNA methylation are detected, sequence data can be compiled, analyzed, and referenced.

The invention also relates to the use of DNA methyltransferases for genotyping specific alleles within genes of interest, genotyping or DNA paint analysis of genomes or specific regions within genomes, and creation of ordered maps for specific regions within genomes. As used here, the term "genotype" means the particular combination of sequence-specific sites present or absent in individual genome or fragment of DNA from an individual genome. The methods of the present invention can be used to determine not only those same DNA methylase sequence-specific recognition sites within a DNA sample, but also those sites associated with the companion restriction endonuclease. DNA MTases also can be used in embodiments whereby point mutations responsible for heritable diseases or traits can be detected, including those which occur at CG' sites. This ability to recognize CG sites is unique to DNA methyltransferases and provides an additional improvement over the use of restriction endonucleases alonein genotyping DNA. Three fourths of known mutations responsible for heritable human diseases occur at CG sites (D. Cooper & H. Youssoufin, "The CpG dinucleotide and human genetic disease", *Human Genetics*, 78:151–165 (1988)). As shown in Table 3, such frequent CG to TG mutations can be detected using M.SsI MTase, which methylates DNA specifically at hypermutable 2 bp CG sites.

In radiometric $^3$H-methyl-incorporation assays, DNA methyltransferase genotyping is carried out using a sequence-specific methyltransferase to transfer $^3$H-methyl groups from $^3$-methyl-SAM to DNA. The incorporation of this radioactively labeled methyl group is monitored by trichloroacetic acid (TCA) precipitation followed by liquid scintillation counting. If several different sequence-specific DNA methylation reactions are carried out, then the pattern of $^3$H-methyl incorporation defines the DNA MTase genotype.

A DNA MTase genotype is a "fingerprint" of DNA based upon the presence or absence of MTase recognition sites. Similarly, a restriction modification (R-M) genotype is a DNA fingerprint in which both restriction (R) and methylase (M) sites are monitored. R-M genotyping of 5' biotinylated allows ordered maps to be rapidly constructed. As a result, alleles or MTase isotypes can be expressed as binary code words. For example, the presence or absence of a single restriction or modification enzyme recognition site can be expressed in binary code as "1" for the presence of the site or "0" for the absence of the site. When looking at the inheritance of an allele associated with a disease state, the resulting DNA can be expressed in ternary code as "0" for homozygous wild type alleles, "1" for heterozygous wild type/disease alleles, or "2" homozygous for the alleles associated with the expression of the disease or trait of interest. This conversion of genotypes into an easily readable digital code allows for larger scale, automated screening procedures to be utilized. Moreover, in the case of radioactive MTase genotyping or combination R-M genotyping, the quantitative assay allows higher order codes to be employed.

Radiometric $^3$H-methyl incorporation can be utilized to genotype entire genomes or smaller DNA fragments of varying lengths. For the analysis of entire genomes, DNA MTases can be used in a method similar to RFLP analysis. In general, RFLP analysis is a technique well known to those skilled in the art. See for example, Erlich, U.S. Pat. No. 4,582,788 issued Apr. 15, 1986 and Gasella, U.S. Pat. No. 4,666,828 issued May 19, 1987, Frosserd, U.S. Pat. No. 4,772,549 issued Sep. 20, 1988, and Frossert, U.S. Pat. No. 4,861,708 issued Aug. 29, 1989, all of which are disclosed for example and are incorporated herein by reference. Broadly speaking, the RFLP technique involves obtaining the DNA to be studied, digesting the DNA with restriction endonucleases, separating the resulting fragments, and then detecting the fragments of altered electrophoretic mbbility associated with those genes of interest.

In the present invention, DNA fragments are detected not by using electrophoretic markers associated with genes, but by utilizing sequence-specific DNA methyltransferases which incorporate radioactively or immunochemically labeled methyl groups into defined 2 to 8 bp DNA sequence-recognition sites.

In the simplest format, DNA is enzymatically methylated; and then the presence or absence of 2 to 8 bp MTase sites is detected either radiometrically or immunochemically. The presence (1) or absence (0) of MTase recognition sites is a "DNA MTase genotype". However more complex "R-M genotypes," based upon combination, of restriction (R) or modification (M) enzymes are possible. For example, DNA can be methylated at specific sites and then digested by a restriction enzymes with a different sequence specificity. After gel electrophoresis and Southern blotting to nylon filters, only those fragments containing sequence-specific radioactively labeled DNA methyl groups are detected via autoradiograms. A variation of this method can be performed by first digesting with a sequence-specific restriction endonuclease followed by incorporation of the radioactively labeled methyl group utilizing a sequence-specific methyltransferase which recognizes a different recognition sequence than the restriction enzyme used.

Another embodiment of the present invention utilizes amplification of desired DNA fragments through the use of standard techniques, such as polymerase chain reaction (PCR). In general, the PCR technique is well known to those skilled in the art and the following references are disclosed for example. The PCR technique is described in Mullis et al., U.S. Pat. No. 4,683,195, issued Jul. 28, 1987, Mullis, U.S. Pat. No. 4,683,202 issued Jul. 28, 1987, Mullis et al., U.S. Pat. No. 4,800,159 issued Jan. 24, 1989, Delfand et al., U.S. Pat. No. 4,889,818 issued Dec. 26, 1989, and Columbus et al., U.S. Pat. No. 4,902,624 issued Feb. 20, 1990, all of which are incorporated herein by reference.

In this embodiment DNA MTase genotyping is carried out using two sequential reactions. First, DNA is amplified using PCR(Mullis et al. 1994):

(1) DNA + primers + dNTP's $\xrightarrow{\text{Tag Polymerase}}$ (DNA)$_n$ + dNTP's Second, amplified DNA is methylated using $^3$H-methyl-SAM and a sequence-specific DNA MTase:

(2) DNA + ³H-methyl-SAM  ³H-methyl-DNA + SAH

This PCR/MTase assay requires neither gel electrophoresis nor hybridization. It is therefore a very fast method for detecting polymorphic sites in DNA. Furthermore, if thermostable polymerase and thermostable MTase enzymes, such as Taq Polymerase and M.TaqI, are used then the DNA amplification and methylation reactions can be coupled in a single reaction mixture. The two major advantages of the coupled PCR/MTase assay are its speed and simplicity. DNA, primers, DNTP's, ³H-methyl-SAM, Taq Polymerase, and a thermostable MTase are placed in a single reaction mixture for thermal cycling. (See FIG. 1) After several cycles of thermal denaturation, annealing, and elongation, the DNA fragments are both amplified and ³H-methylated at defined sequences. H-methyl-DNA can then be TCA precipitated, spotted onto a filter paper, washed, and counted. These counts can be expressed as raw data (cpm) or mathematically as either a binary code or a ternary code as described above.

As an alternative to PCR amplification by thermocycling, it is possible to methylate DNA amplified isothermally at 37° C. by strand displacement amplification (SDA) (Walker et al., 1992). In SDA, the template DNA is mixed with 4 primers, dCTP, dTTP, dGTP, and α-S-dATP at 94° C. Following denaturation at 94° C., HincII restriction endonuclease and Klenow exo⁻ Polymerase are added whereby α-S-substituted DNA is repeatedly nicked and amplification occurs isothermally at 37° C. by strand displacement.

It is also possible to couple SDA amplification and DNA methylation in a single reaction mixture by a modification of the above procedure. In this case, a DNA MTase and ³H-SAM could be added at the same time as the HincII restriction endonuclease and the Klenow exo-Polymerase. This would allow for methylation to occur in the same reaction mix as the amplification of the DNA. (See FIG. 2) A large number of sequence-specific DNA MTases are suitable for isothermal SDA/MTase genotyping because thermal stable enzymes are not required.

In both the PCR/MTase assay and the SDA/MTase assay, the presence or absence of a sequence-specific mutation or variation can be detected by the presence or absence of radioactively labeled methyl groups following TCA precipitation, spotting onto filter paper, washing, and scintillation counting.

In a more preferred embodiment of this method, short (30–100 bp) PCR products are used. In RFLP mapping of amplified DNA, the size of the amplicon is usually constrained by the need for fragments that are separable by gel electrophoresis and can be detected by ethidium bromide staining. DNA fragments are typically several hundred base pairs long. However, in DNA MTase genotyping, improved speed and sensitivity are possible when short (30–100 bp) amplicons are methylated.

The method is faster when amplification of short PCR or SDA products is used. For example, if a central 20 bp polymorphic DNA sequence is amplified using two 20-mer primers, then the size of the resulting amplicon is 60 bp (20 bp from each primer plus 20 bp of amplified DNA). At an elongation rate of about 50 nucleotides per second at 72° C. for TAQ Polymerase, only 1 to 2 seconds are needed to replicate the 60 bp amplicon during each cycle of amplification. In contrast, typical PCR thermal cycling products require elongation times of approximately 1 minute or more per cycle.

In addition, because the molecular weight of the amplified DNA product is smaller, its molar concentration is proportionately higher. For example, 1 μg of a 200 bp-DNA fragment in a 25 gl reaction has a molar concentration of approximately 3 μM, but 1 μg of a 60 bp fragment in the same volume has a concentration of approximately 9 μM. If each of these DNA fragments has a single MTase recognition site, then the number of methyl groups incorporated into this shorter 60 bp fragment will be three-fold greater. In short, the use of short PCR products allows for faster amplification times and improved sensitivity as evidenced through stronger signals due to higher molar concentration.

Another embodiment of the present invention is the use of non-radioactive immunochemical detection of methylated DNA. Prior to the present invention, the use of immunochemical detection following in vitro DNA methylation was unknown. Immunochemical detection methods are well known to those of skill in the art and the creation of antibodies, including monoclonal antibodies, to modified nucleotides has been the subject of many publications. See, e.g. D. C. Eichler & D. G. Glitz, "Nucleotide-Specific Antibodies as Potential Blocking Agents in the Structural Analysis of Nucleic Acids", 335 BBA 303–317 (1974); C. W. Achwal and H. S. Chandra, "A sensitive immunochemical method for detecting 5mC in DNA fragments", *FEB Letters*, 150:469–472 (1982); B. F. Erlanger & S. M. Beiser, "Antibodies to methylated bases in nucleic acids", *Proc. Nat Acad Sciences, USA*, 52:68 (1964); Brooks et al., "An improved method for the purification of IgG monoclonal antibodies from culture supernatants", *Journal of Immunological Methods*, 155:129–32 (1992); Sano et al., "Detection of heavy methylation in human repetitive DNA subsets by a monoclonal antibody against 5-methylcytosinen", *Biochemica et Riophysica Acta.*, 951:157–65 (1988). A variety of non-radioactive formats are currently available including the use of infra-red tags, fluorescent dyes, chemiluminescence, and alkaline-phosphatase conjugated antibodies. A more preferred embodiment utilizes specific antibodies which can be used to immunochemically detect $^{6m}$A-or $^{4m}$C-methylated DNA. Although there are several references which teach the creation of antibodies to $^{5m}$C, (See eg: C. W. Achwal & H. S. Chandra, "A Sensitive Immunochemical Method for Detecting 5 mC in DNA Fragments", Vol. 150 No. 2, *FEBS Letters* 469–472; C. W. Achwal et al., "Estimation of the Amount of 5-Methylcytosine in Drosophila Melanogaster DNA by Amplified ELISA and Photoacoustic Spectroscopy", Vol. 3 No. 2 *EMBO Journal*, 263–266 (1984); J. A. Vilpo et al., "Radioimmunoassay of 5-Methyl-2'-Deoxycytidine: A Method for the Quantification of DNA Methylationt", 75 *Journal of Immunoloical Methods*, 241–246 (1984)), it was a surprising result to find poor immuno-reactivity in anti-$^{5m}$C antibodies in the present invention due to poor signal-to-noise ratio. In addition, the creation of $^{5m}$C antiserum in rabbits has proven to be very difficult. However, this technical problem may be due to a tolerance-type lack of response in the rabbits after injection of the $^{5m}$C conjugates. Therefore, in some examples of the present invention, the use of anti-$^{6m}$A- or anti-$^{4m}$C-antiserum was preferred. One skilled in the art could appreciate that anti-$^{5m}$C antibodies suitable for immunostaining of $^{5m}$C methylated DNA are also possible.

In one embodiment utilizing immunochemical detection methylated DNA fragments can be adhered to a solid matrix. For example, the methylated DNA fragments can be run out on an agarose gel and adhered to a solid nylon membrane using Southern blotting methods. Another example includes the use of methylated DNA fragments where one of the primers used to create the methylated amplicon was biotinylated and this resulting biotinylated fragment is captured on a Streptavidin-coated ELISA plate (Boehringer). The presence of the methylated nucleoside can then be detected utilizing anti-$^{6m}$A or anti-$^{4m}$C immune serum followed by an anti-anti-$^{6m}$ antiserum IgG or anti-anti-$^{6m}$ immune serum which has been conjugated with either alkaline phosphatase or peroxidase. Colorimetric assays can then be conducted. In the above examples, NBT/BCIP substrate for alkaline-phosphatase would be added to the nylon membrane whereby blue bands, or in the case of dot blots--blue spots, on the white background of the nylon filter would be observed. In the case of a Streptavidin coated ELISA plate, peroxidase-conjugated goat anti-rabbit IgG would be detected through the addition of ABTS® (Boehringer) whereby the resultant color would bep measured at 450 nm using an ELISA plate reader.

Yet another embodiment of the present invention utilizes the use of DNA methylation and restriction endonuclease digestion followed by immunochemical detection or "DNA paint". In the "DNA paint" format, DNA is first methylated at specific sites and then digested by restriction enzymes which possess a different sequence specificity. Conversely, the DNA can be first restriction endonuclease digested followed by methylation at different sequence-specific sites. After digested/methylated DNA undergoes gel electrophoresis and Southern blotting to nylon filters, only those fragments containing sequence-specific DNA methyl groups are immunochemically detected as described above.

Yet another embodiment of the invention utilizes an anchored PCR format in which biotinylated primers in combination with DNA MTases and restriction endonucleases are used. One advantage of using a biotinylated anchored PCR format is that generation of ordered maps can be created by using a solid matrix such as Streptavidin-coated magnetic beads (MGP, Lincoln Park, N.Y.). In this method, the DNA is PCR amplified using a 5' biotinylated forward primer and non-biotinylated reverse primer. The resulting amplicons are then methylated using sequence-specific DNA methyltransferases and $^3$H-methyl-SAM. If appropriate buffer conditions are employed, the DNA fragment can be enzymatically $^3$H-methylated and digested with sequence-specific endonucleases in the same reaction mix. Each amplicon is anchored to Streptavidin-coated magnetic beads via the biotin present in the forward primer. If a restriction enzyme cuts between the $^3$H-methyl site and the biotin anchored 5' end then the $^3$H-methyl group is no longer attached to the bead. The $^3$H-methyl groups in the remaining DNA are measured by TCA precipitation and liquid scintillation counting as described above. Ordered maps are constructed for restriction enzymes (R) and MTases (M) using an (R+1)×(M+1) coding. By looking at the results in matrix format with restriction endonucleases along one axis and methyltransferases along the opposite axis, one can determine the order of the restriction and modification sites as oriented by the 5' biotinylated forward primer.

Another embodiment of this anchored PCR format utilizes SPA (scintillation proximity assay) beads. N. Bosworth & P. Towers, "Scintillation Proximity Assay", *Nature* 341:167–168 (1989), incorporated herein by reference. This method is even faster than the magnetic bead detection of $^3$H-methyl-DNA because removal of $^3$H-methyl-SAM or other sample processing steps are not required prior to the detection of the H$^3$C-labeled DNA. In SPA, reaction products labeled with low energy beta emitters such as $^3$H are captured on the surface of Streptavidin-coated fluoromicrospheres (SPA beads). Since beta particles from tritium decay travel only about 1 micrometer in water, unincorporated $^3$H-labeled precursor molecules are, on the average, too far away from the SPA beads to excite fluorescence. However, biotinylated $^3$H-methyl labeled DNA reaction products are tightly bound to Streptavidin SPA beads and cause the scintillation beads to emit light. SPA assays are extremely fast because no sample processing or separation of unincorporated radiolabeled precursors is required. In an SPA format, $^3$H-methyl-SAM does not need to be removed. Time consuming, labor intensive steps such as TCA precipitation, filter processing, and the addition/disposal of scintillation fluid are unnecessary. If biotinylated primers are used for PCR (or SDA) amplification, followed by sequence-specific methylation using $^3$H-methyl-SAM, then biotinylated $^3$H-methyl-DNA can be captured on Streptavidin beads and counted directly as an aqueous suspension. Using coupled DNA amplification/methylation reactions and SPA detection, it is possible to diagnose biologically and medically important pathogens or traits in less than thirty minutes. If combinations of restriction enzymes (R) and methylases (M) are employed in an anchored Streptavidin-SPA bead format, then ordered maps of R-M sites in 5' biotinyulated DNA can be rapidly constructed. Binary (0, $\geq$1) or ternary (0, 1, $\geq$1) signal encoding of bound $^3$H-methyl-DNA signals is readily decoded using an (R+1)×(M+1) array.

It is to be understood that one of skill in the art can utilize the knowledge of DNA methyltransferases and restriction endonucleases and the methylation and restriction sites of those MTases and endonucleases in conjunction with the teachings of the present invention to analyze and/or exploit the DNA genotype of any sequence of DNA underlying different methyltransferase/endonuclease/genome or gene combinations or methyltransferase/genome or gene combinations. It is also to be understood that the application of the teachings of the present invention to a specific problem or environment will be within the capabilities of one having ordinary skill in the art in light of the teachings contained herein. It is to be further understood that all citations to articles, patent applications, patents, etc., herein are hereby expressly incorporated by reference. The examples of the products and processes of the present invention appear in the following examples.

EXAMPLE 1

DNA MTase Genotyping of pBluescript DNA

A preliminary experiment was carried out to test the feasibility of DNA MTase genotyping using pBluescript plasmid (Stratagene) in a simple model system. T3 and T7 DNA sequencing primers (Stratagene) were used to amplify 10 ng of the polylinker region of pBluescript SK+DNA using Taq Polymerase. About 1 µg of PCR-ampltfied plasmid DNA was untreated or else digested by EcoRI, BamHI, or PstI endonucleases (10 units, 2 hours). These DNA's were then phenol extracted, alcohol precipitated in 1.5 ml Eppendorf tubes and resuspended in 30 µl of 15 mM Tris-HCl, pH7.5, 5 mM EDTA, 100 µg/ml BSA, approximately 2 mM $^3$H-methyl-SAM (New England Nuclear, approximately 85 Ci/mmole). 5 units of M.EcoRI or M.BamHI was added and methylation was carried out for one hour at 23° C. The amount of $^3$H-methyl-DNA was measured by TCA precipitation and liquid scintillation counting. M. Nelson & M. McClelland, "Purification and Assay of Type II DNA Methylases", *Methods in Enzymology* 155:332–341 (1987), incorporated herein by reference.

This initial feasibility experiment shows that the presence or absence of DNA MTase sites in PCR-amplified DNA can be determined by $^3$H-methyl incorporation assay.

TABLE 1

DNA MTase Genotyping of 191 Base Pair PCR Amplified Polylinker Region of pBluescript DNA

| | TCA Precipitable $^3$H-Methyl-DNA Counts per Minute | | |
|---|---|---|---|
| DNA Pre-Digested by | No MTase | M.EcoRI | M.BamHI |
| Undigested | 574 | 85,043 | 69,719 |
| EcoRI | 750 | 770 | 1306 |
| BamHI | 661 | 32,830 | 999 |
| PstI | 836 | 27,674 | 817 |

Secondly, the results of this DNA MTase genotyping experiment conclusively show that the specificity of DNA MTase genotyping is the same as that of RFLP mapping: DNA sites precut by EcoRI or BamHI restriction endonucleases cannot be methylated by M.EcoRI or M.amHI MTases, respectively. (See Table 1). Third, the signal-to-noise performance using a $^3$H-methyl-DNA incorporation assay is excellent. Using M.EcoRI (GA$^{6m}$ATTC) or M.BamHI (GGAT$^{4m}$CC), sequence-specific incorporation of 70,000 to 85,000 cpm of $^3$H-methyl groups into 1 μg of PCR amplified 191 base paired DNA is observed against a background of approximately 600 to 800 counts per minute (cpm). For approximately 200 base pair amplicons, as little as 1 μg of PCR amplified DNA could be easily detected. Even greater sensitivity can be achieved if shorter amplicons are used. Finally in some cases, predigestion by an endonuclease interferes with methylation by a DNA MTase that has a different sequence specificity. For example, pBluescript DNA that has been digested by EcoRI is methylated poorly by M.BamHI. The proximity of "frayed" EcoRI DNA ends to M.BamHI MTase sites interferes with methylase catalysis. This steric effect allows the relative locations of certain DNA MTase sites to be identified and can be used to confirm the authenticity of PCR products.

EXAMPLE 2

DNA MTase Genotyping of a Heritable Human Disease

MTase genotyping technique can be used to rapidly diagnose heritable human diseases, such as neonatal alloimmune thrombocytopenia (NAT); a childhood blood disease which affects ~1:800 babies.

NAT is a blood-borne maternal-fetal immune disease that affects approximately 40% of babies in neonatal intensive care units. In NAT, the mother produces antibodies against her child's blood platelet antigens. Affected infants are born with bruises and are prone to hemorrhages. If left untreated, about one-fourth of these babies die of cranial hemorrhages or are neurologically impaired (Castle et al, 1986). However, if properly diagnosed, NAT infants can be treated by transfusion or washed (antibody-free) blood platelets from their mothers (Abnor et al., 1969).

The mother of an NAT child is deficient in platelet glycoprotein antigens of the GPIb/GPII/GPIIIa complex; but the baby inherits genes for immunoreactive platelet antigens from its father. Four alleles of human platelet antigen (HPA) are known: HPA-1 (Zw) HPA-2 (Ko) HPA-3 (Bak) or HPA-4 (Yuk).

In mutant HPA-4 (Yuk$^{b/b}$) homozygotes the GPIIIa glycoprotein gene is mutated from TGM at position 526 to TGCA. Like most mutations responsible for heritable human diseases (Cooper & Youssoufian, 1988), this mutation is due to $^{5m}$CG→TG deamination on the lower DNA strand. The loss of CG (M.SssI) site from Yuk$^a$ DNA corresponds to a gain of a TGCA (M.S RI site)in Yuk$^b$ DNA. As a result, wild type Yuk (Yuk$^a$) and mutant (Yuk$^b$) alleles can be genotyped by PCR amplification and DNA methylation using M.SssI and/or M.CviRI. The two step DNA amplification/methylation method requires less than two hours.

DNA was isolated from blood samples of wild type (Yuk$^{a/a}$) and homozygous (Yuk$^{b/b}$) patients containing mutations in the GPIIIa glycoprotein gene. These DNA's had previously been typed by restriction isotyping (RFLP analysis) using restriction enzyme CiRI (TGC). PCR amplification was carried out using 5'-GGTGGGAGAAGAAGATAAAAAG-3' (SEQ ID NO: 3) and 3'-CCAGGTTCAGGACCAAGGAT-5' (SEQ ID NO: 4) primers. A 362 base pair DNA fragment spanning the yuk allele of the GPIIIa glycoprotein gene was amplified using 30 cycles of Taq Polymerase denaturation/annealing/elongation. (See FIG. 3A). About 2 μg of PCR-amplified Yuk DNA was alcohol precipitated and resuspended in 30 μl of TE buffer pH 8.0. 5 μl (about 0.25 μg) of this amplified Yuk$^{a/a}$ or Yuk$^{b/b}$ DNA was added to a 30 μl reaction containing 50 mM Tris-acetate, PH 7.5, 5 mM EDTA, 100 μg/ml BSA, and approximately 2 μM of $^3$H-methyl-SAM (New England Nuclear, approximately 85 Ci/mmole). 5 units of either M.CviRI (TGC$^{6m}$A) or M.HaeIII (GG$^{5m}$CC) MTase was added, and DNA methylation was carried out for 2 hours at 23° C. TCA precipitation and liquid scintillation counting were carried out as described by Nelson & McClelland (1987) (See Table 2).

TABLE 2

DNA MTase Genotyping of 362 Base Pair PCR Amplified Yuk$^{a/a}$ or Yuk$^{b/b}$ Alleles of Neonatal Alloimmune Thrombocytopenia patients

| | TCA-Precipitable $^3$H-Methyl-DNA Counts per Minute | | |
|---|---|---|---|
| DNA | No MTase | M.CyiRI | M.HaeIII |
| pUC19 (Control) | 615 | 118,417 | 26,156 |
| Yuk$^{a/a}$ | 472 | 506 | 36,442 |
| Yuk$^{b/b}$ | 501 | 12,241 | 34,217 |

DNA MTase genotyping can clearly be used to genotype heritable diseases. This experiment shows that the speed, accuracy, and sensitivity of MTase genotyping are suitable for diagnosing many traits of medical or economic interest. In the present example, PCR/MTase genotyping was able to detect a point mutation in a single copy gene responsible for a heritable human disease. The presence of a TGCA site and PCR-amplified Yuk$^{b/b}$ DNA is easily distinguished from its absence in Yuk$^{a/a}$ DNA by M.CviRI MTase genotyping.

In addition, the signal-to-noise performance is excellent. Using approximately 0.25 μg of 362 bp amplified DNA from human blood, 12,241 cpM of $^3$H-methyl-DNA is observed in Yukb/b DNA which contains one TGCA site. Only 506 cpm of $^3$H-methyl-DNA are observed in Yuk$^{a/a}$ DNA, which has no TGCA sites. If shorter (60–70 base pair) PCR amplicons are employed, then even greater (5–6 fold greater) sensitivity should be possible. Under "short PCR" conditions, it should be possible to easily discriminate Yuka/a, Yukb/b, and heterozygous Yuka/b 3H-methyl-DNA's as signals of approximately 500 cpm, approximately 60,000 counts per minute, or approximately 30,000 counts per minute, respectively, would result. For example, using PCR primers 5'-GAACCTGGGTACCAAGCTTGGC-3' and 3'-GTGGTCATTGGACTCCTAACCG-5'; the 61 bp fragment spanning the M.CviRI and M.SssI sites can be amplified (See FIG. 3B).

Finally, the success of MTase genotyping of NAT patients is of particular interest because the use of short PCR conditions and/or the use of both M.CviRI and M.SssI should allow the diagnostician to determine whether the allele composition is homozygous Yuk$a/a$, homozygous Yuk$b/b$, or heterozygous Yuk$^{a/b}$. The method currently being used in NAT diagnosis utilizes restriction endonuclease enzymes to digest fragments for fingerprinting using gels and/or Southern blots. In addition to being slow, a severe drawback results from this use of restriction endonucleases alone when incomplete digestion of a homozygous Yuk$b/b$ DNA gives the appearance of a Yuk$a/b$ carrier. (See FIGS. 4A and 4B) When a patient is determined to be Yuk$a/b$, no therapy or platelet transfusion is given. This can have tragic results. If an affected Yuk$b/b$ infant does not receive a proper therapy, then it may die. As mentioned above, affected infants are prone to hemorrhages and can die of cranial hemorrhaging or are neurologically impaired. However, with the use of the present inventive method a clearcut genotype can rapidly and accurately be obtained. Using quantitative PCR/MTase genotyping, the different levels of $^3$H-methyl incorporation into DNA by M.CviRI (TGC$^{6m}$A) or M.SssI ($^{5m}$CG) can be encoded using a ternary (0,1,2) code. For example, using approximately 1 $\mu$g of amplified htman DNA (a/a=0, a/b=1, and b/b=2), the difference between a signal level of 1 and 2 is tens of thousands of $^3$H-methyl cpm. By ternary encoding, an algebraic distance of two can be achieved between a/a, a/b, and b/b genotypes (See Table 3). Systematic error detection is possible, so that misdiagnosis of a/b heterozygote carriers for b/b homozygotes is much less likely. R. W. Hamming, *Coding and Information Theory*, 2 nd Ed., Prentice-Hall, Englewood Cliffs, N.J. (1986), incorporated herein by reference.

TABLE 3

Ternary (0, 1, 2) Signal Encoding of DNA MTase Genotypes

| DNA | DNA MTase Genotype No MTase Control | M.SssI ($^{5m}$CG) | M.CviRI (TGC$^{6m}$A) |
|---|---|---|---|
| Wild type Yuk$^{a/a}$ | 0 | 2 | 0 |
| Heterozygous Yuk$^{b/b}$ | 0 | 1 | 1 |
| Homozygous Yuk$^{b/b}$ | 0 | 0 | 2 |

Hypothetical cpm ranges:
0:$^3$H-methyl cpm ≦ 800
1:800 < cpm < 10,000 cpm
2:cpm > 10,000

EXAMPLE 3

Radiometric Detection and Ordered Maps in <30 Minutes

In classic RFLP mapping (Bottstein et al., 1980), DNA fragments must be long enough to contain polymorphic 4 to 6 bp restriction sites and to be stained by ethidium bromide after gel electrophoresis. However, since MTases do not cut the sugar-phosphate backbone of DNA, in DNA MTase genotyping, there are no DNA fragments to be separated. Therefore, gel electrophoresis and ethidium bromide staining are unnecessary. Improved speed and sensitivity are possible when relatively short (30 to 100 bp) amplicons are methylated: the shorter the better. In simple terms, if the molecular weight of a DNA fragment is smaller, then its molar concentration is higher. For example, 1 $\mu$g of a 300 bp DNA fragment in a 25 $\mu$l reaction volume has a concentration of ~2 $\mu$M, but 1 $\mu$g of a 100 bp fragment in the same reaction volume has a concentration of ~6 $\mu$M. If each of these DNA fragments has a single MTase recognition site, then the $^3$H-methyl incorporation into the shorter 100 bp fragment will be three-fold greater.

As an added benefit, amplification of short PCR products is also faster because thermocycle times can be reduced to a few seconds per cycle. This time can be further reduced by using a hot-air thermocycler and a rapid sample preparation protocol. Sequence-specific DNA 3 H-methylation can be conveniently detected in a homogenous solid phase Scintillation Proximity Assay (SPA; Bosworth and Towers, 1989) using a biotinylated PCR primer and Streptavidin-coated SPA beads (Amersham, Arlington Heights, Ill.). Radiometric DNA MTase Genotyping (DMG) has been used diagnose viral pathogens and to detect genetic polymorphisms in less than 30 minutes.

Moreover, if combinations of DNA MTases (M) and restriction endonucleases (R) are employed in an anchor-dependent SPA bead detection format, then ordered physical maps can be constructed in a few minutes without the need for electrophoresis. Radiometric DNA MTase Genotyping requires three steps: (1) PCR-amplification of DNA, (2) 3 H-methylation using a sequence-specific MTase, (3) capture of $^3$H-methyl-DNA on SPA beads. The presence (binary 1) or absence (binary 0) of any particular DNA MTase recognition site is easily determined in a few minutes. When a "universal buffer" such as KGB is employed, all three steps can be carried out sequentially in the same reaction buffer. (McClelland et al., "KGB: A single buffer for all restriction endonucleases", *Nucleic Acid Research*, 16(1):364 (1988).) This simple 1–2–3 method requires only 20 to 30 minutes to perform manually; and probably less than 15 minutes in automated analysis. For example, as shown in Table 4 and FIG. 5, ordered maps of Herpes Simplex Virus DNA from HSV-1 and HSV-2 can be constructed in about 30 minutes using a 5' biotinylated primers, various combinations of restriction enzymes and MTases, and rapid Streptavidin-SPA bead detection.

A 103 b.p. amplicon obtained by PCR amplification of 2 ng of HSV-1 (SEQ ID NO: 5) or HSV-2 (SEQ ID NO: 6) DNA with a 5' biotinylated reverse primer was $^3$H-methylatedusing 10 U M.MspI (CCGG), M.TaqI (TCGA), or M.HhaI (GCGC) MTases in the presence of ~2 $\mu$M $^3$H-methyl-SAM. As noted, DNA was also digested using 10 U restriction endonucleases MspI (C↓CGG), RsaI (GT↓AC), or BstUI (CG↓CG). The resulting 5' biotinylated $^3$H-methylated/restriction digested DNA was mixed with Streptavidin-SPA beads (Amersham), suspended in ~1 ml phosphate-buffered saline and counted for bound $^3$H-methyl-DNA cpm using a Packard scintillation counter (See Table 4).

TABLE 4

Ordered Maps* of Short PCR-Amplified HSV-1 and HSV-2 DNAs Using Combinations of DNA MTases and Restriction Endonucleases

| DNA source | DNA MTase | Restriction Endonuclease | $^3$H-methyl DNA cpm | Binary signal (>10,000 cpm = 1, ≦ 10,000 cpm = 0) |
|---|---|---|---|---|
| HSV-1 | None | None | 425 | 0 |
| HSV-2 | None | None | 225 | 0 |
| HSV-1 | M. Taq I | None | 9,056 | 0 |
| HSV-2 | M. Taq I | None | 128,236 | 1 |
| HSV-1 | M. Taq I | Rsa I | 1,667 | 0 |
| HSV-2 | M. Taq I | Rsa I | 5,550 | 0 |
| HSV-1 | M. Taq I | Msp I | 1,667 | 0 |

TABLE 4-continued

Ordered Maps* of Short PCR-Amplified HSV-1 and HSV-2 DNAs Using Combinations of DNA MTases and Restriction Endonucleases

| DNA source | DNA MTase | Restriction Endonuclease | $^3$H-methyl DNA cpm | Binary signal (>10,000 cpm = 1, ≤ 10,000 cpm = 0) |
|---|---|---|---|---|
| HSV-2 | M. Taq I | Msp I | 9,319 | 0 |
| HSV-1 | M. Hha I | None | 8,963 | 0 |
| HSV-2 | M. Hha I | None | 246,516 | 1 |
| HSV-1 | M. Hha I | Rsa I | 3,565 | 0 |
| HSV-2 | M. Hha I | Rsa I | 122,134 | 1 |
| HSV-1 | M. Hha I | Msp I | 1,061 | 0 |
| HSV-2 | M. Hha I | Msp I | 5,243 | 0 |
| HSV-1 | M. Msp I | None | 166,300 | 1 |
| HSV-2 | M. Msp I | None | 115,020 | 1 |
| HSV-1 | M. Msp I | BstU I | 2,866 | 0 |
| HSV-2 | M. MSP I | BstU I | 1,005 | 0 |

*See FIG. 5

By measuring at the $^3$H cpm (presence of MTase site >10,000 $^3$H-methyl-DNA, absence of MTase site ≤10,000 $^3$H-methyl DNA cpm), relative locations of restriction enzyme sites and methylation sites in relation to the 5' biotinylated end bound to the SPA Bead can be determined. For example, a comparison of the cpm for M.TaqI $^3$H-methyl labeled HSV-1 and HSV-2 when uncut and cut with RsaI shows the HSV-1 does not have a M.TaqI (TCGA) site and that RsaI restriction enzyme site (GTAC) is between the M.TaqI site and the 3' SPA-Bead of HSV-2. Note the immediate proximity of the M.HhaI site and the RsaI restriction enzyme site reduces the efficiency of the RsaI digest and only cuts about half the time. By comparing the results in Table 4 to the DNA sequence found in FIG. 5, it is clear that methyltransferase ordered mapping is a quick, accurate and useful procedure. It can also be seen that monitoring the absence or presence of a DNA site by counting $^3$H-methyl-DNA bound to a solid phase bead is a very useful and versitile tool for quick screening of samples and is conducive to large scale analysis of multiple samples.

EXAMPLE 4

Non-Radioactive Lmmunochemical Detection of Methylated DNA

DNA MTase genotyping can also be carried out in a nonradioactive format. In particular, specific antibodies have been used to immunochemically detect enzymatically methylated $^{6m}$A-labeled DNA. Similar immunochemical detection procedures could also be used to detect $^{5m}$C or $^{4m}$C methylated DNA.

Rabbit antibodies to $^{6m}$A were prepared by the method of B. F. Erlinger & S. M. Beiser, "Antibodies to methylated bases in nucleic acids", *Proc. Nat, Acad. Sciences USA* 52:68 (1964) as modified by B. D. Stollar, "The Experimental Induction of Antibodies to Nucleic Acids", *Methods in Enzymology* 70:70–85 (1980), both incorporated herein by reference. Periodate-oxidized 6 A ribonucleosides were coupled to hemocyanin at pH 9.5, reduced using 0.1 M NaBH$_4$, and dialyzed against 0.1 M NaHCO$_3$ (pH 8.5) and then against distilled H$_2$O. The resulting $^{5m}$C- and $^{6m}$A-hemocyanin conjugates were injected into rabbits. About 30 ml of blood was collected from hyper-immunized animals, and clarified in anti-$^{5m}$C and anti-$^{6m}$A sera were frozen at −20° C.

The specificity of rabbit anti-$^{6m}$A serum for $^{6m}$A residues in UV-irradiated DNA bound to nylon sheets was tested by immunochemical staining of in vivo methylated (or control unmethylated) DNA's, using alkaline-phosphatase conjugated goat anti-rabbit IgG.

Various dilutions (0/1 ng to 100 ng) of in vivo $^{6m}$A-methylated Chlorella virus NY-s (37% $^{6m}$A), phage λdam$^+$, (1.5% $^{6m}$A) and plasmid pBR322 dam$^+$DNAs (1.5% $^{6m}$A) were spotted onto nylon Hypobond™ membranes and uv-crosslinked prior to immunochemical staining. The membrane was blocked for one hour using 10 ml of (100 mM Tris, pH 7.6, 100 mM NaCl, 10% nonfat milk). 100 µl of 1/500 diluted rabbit anti-$^{6m}$A antisera was then added in fresh blocking solution, followed by incubation for 30 minutes at 23° C. After four 5 minute washes in blocking buffer, 100 µl of alkaline-phosphatase conjugated goat anti-rabbit secondary antibody (Vector Labs) was added, followed by incubation for 20 minutes at 23° C. After four 5 minute washes to remove excess enzyme-antibody conjugate, BCIP substrate (KPL Labs) was added and the reaction was developed for 5 minutes at 23° C.; and then stopped by placing the filter in distilled H$_2$O. (Results from this initial immunochemical staining experiment are not shown.) Two conclusions were drawn from this experiment: First, $^{6m}$A methylated DNA can be detected immunoenzymatically as dark spots on a white or light purple filter background using a 1/500 diluted anti-$^{6m}$A immune serum. As little as 1 nanogram of heavily methylated NYS1 DNA (37% $^{6m}$A) can be detected. When sequence-specific DNA methylation occurs at G$^{6m}$ATC (dam$^+$) sites (1.5% $^{6m}$A), as little as 10 ng of PBR322 (dam$^+$) DNA or 20 ng of λ (dam$^+$) DNA can be detected. Second, the background binding of anti-$^{6m}$A serum to methyl deficient dam- DNA is barely detectable. Phage λ(dam$^-$) and plasmid PBR322 (dam$^-$) DNA's are essentially not stained using the anti $^{6m}$A antibody. This light background staining of 200 ng of λ(dam$^-$) and PBR322 (dam$^{31}$) DNA's can probably be eliminated by purification of anti-$^{6m}$A immunoglobins or with the use of monoclonal antibodies.

In vivo methylated Chorella virus DNA was obtained from NY2A (37% $^{6m}$A) and PBCVI (3%$^{6m}$A) strains as described in Nelson et al., 1993. T7 bacterial phage DNA (unmethylated) was obtained from Sigma Chemicals, St. Louis, Mo. Various dilutions of methylated or unmethylated DNA was spotted onto nylon Hypobond™ filters and UV irradiated for two minutes. The membranes were incubated in blocking solution (100 mM Tris pH 8'200 mM NaCl and 1 mM EDTA containing 10% nonfat milk) overnight at 4° C. The membrane was washed for one hour at room temperature in 10 mls of the 1:500 dilution of anti-$^{6m}$A rabbit immune serum (Megabase Research Products, Lincoln, Nebr.) in the above blocking solution. Filters were washed 3 times with 100 mM Tris pH 8, 200 mM NaCl, 100 mM EDTA, 0.5% Tween 20, and then 3 times with the same solution without detergent. A 1/500 dilution of alkaline-phosphatase conjugated goat anti-rabbit IgG antiserum (Vector Labs, Burlingame, Calif.) was used as a secondary antibody. After washing as described above, NBT/BCIP substrate for alkaline-phosphatase (KPL Laboratories, Gaithersburg, Md.) was added.

Figure 6:
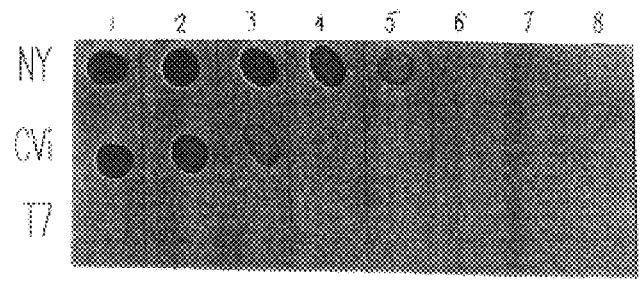
FIG. 6 is a photograph of a nylon membrane "dot blot" showing alkaline-phosphatase immunostaining of $^{6m}$A-methylated DNA using rabbit anti-$^{6m}$A immunoglobin followed by alkaline-phosphatase goat anti-rabbit antibodies and developed with BCIP substrate. Various amounts of $^{6m}$A-methylated Chlorella virus NY2A DNA, $^{6m}$A-methylated Chlorella virus PBCVI DNA or unmethylated bacteriophage T7 DNA were spotted onto the nylon sheet (left to right: 10 ng, 1 ng, 100 pg, 10 pg, 1 pg, 100 fg, 10 fg, 1 fg of DNA). The DNA was fixed to the nylon by UV light treatment and then the methylated DNA was immunochemically detected. This figure shows clearly that $^{6m}$A methylated NY2A (37% $^{6m}$A) and PBCVI (3% $^{6m}$A) DNAs are specifically immunostained; in contrast unmethylated phage T7 DNA does not stain using anti-$^{6m}$A antibodies.

Methylated DNA is detected as purple spots on white nylon filter background. FIG. 6 is a photograph showing the immuno staining results. The first row of DNA is the NY2A (NY), the second row is the PBCVI(cvid), the third row is the T7 bacterial phage (T7). Columns 1–8 are DNA in the amounts of 10 ng, 1 ng, 100 pg, 10 pg, 1 pg, 100 fg, 10 fg, and 1 fg, respectively. The results of this experiment show that $^{6m}$A-methylated DNA can be specifically detected using 1/500 diluted anti-$^{6m}$A immune serum. As little as 1 picogram of methylated NY2A DNA (37% $^{6m}$A) and 10 picogram of PBCVI (3% $^{6m}$A) can be detected. In addition, the results show no background binding of anti-$^{6m}$A serum to unmethylated DNA is detectable using this method. Finally, the results show the anti-$^{6m}$A serum can detect below the limit of detection of ethidium bromide: as little as 1 picogram of $^{6m}$A methylated DNA is detectable.

EXAMPLE 5

Restriction Digestion Followed by Immunochemical Detection

A more sophisticated immunochemical detection scheme for staining DNA fragments which are internally methylated between the 5' and 3' ends relies on Southern blotting. DNA is first methylated at specific sites and then digested by restriction enzymes which have a different sequence specificity. After gel electrophoresis and Southern blotting to nylon filters, only those fragments containing sequence-specific DNA methylation groups are immunochemically stained. In simple terms, DNA restriction fragments from endonuclease #1 can be "painted" at specific sites using MTase #2.

DNA is methylated using $^{6m}$A-specific DNA MTases in (50 mM Tris PH7.5, 5mM EDTA, 100 $\mu$M SAM). In vitro methylated DNA is then digested using one or more restriction endonucleases. The DNA is separated on a it agarose gel (Agarose GTG, FMC, Rockland, Me.) and stained with ethidium bromide and Southern blotted onto a nylon membrane which is UV crosslinked prior to immunochemical staining. The blotted DNA is later immunochemically detected with a rabbit anti-$^{6m}$A antisera and a goat anti-rabbit antiserum (Megabase, Lincoln, Nebr.) as described in Example 4.

Figure 7A:
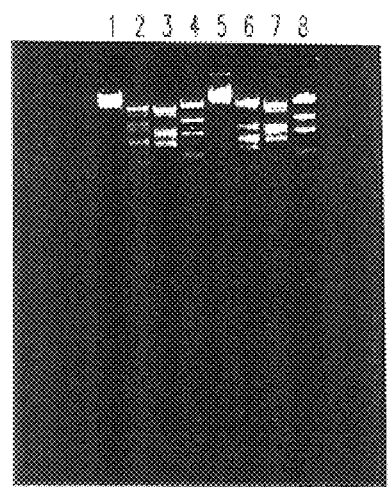
FIGS. 7A and 7B show an early "purple DNA Paint" experiment.
Figure 7B:
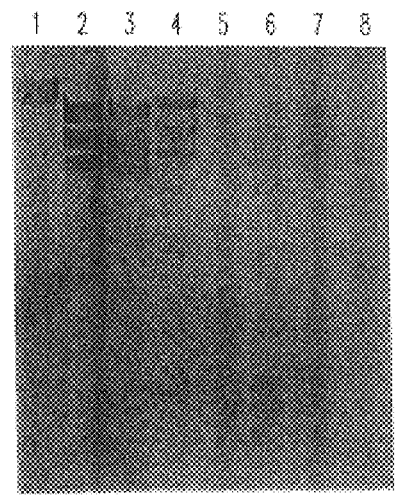

In FIGS. 7A and 7B a preliminary experiment is shown in which lambda dam+or dam–DNA was digested with restriction endonucleases. One microgram of lambda DNA was digested for 2 hours at 37° C. with 15 units of EcorI, BamHI or HindIII restriction endonucleases in a 20 $\mu$l volume. The reaction mix was mixed with dye-EDTA stop buffer and electrophoresed for 4 hours at 60 Volts in a 1 t agarose gel.

FIG. 7A is a photograph of the gel used for transfer showing the $\lambda$ (dam$^+$) DNA in lanes 1–4 undigested, EcoRI digested, BamHI digested and HindIII digested respectively; Lanes 5–8 of FIG. 7A show the $\lambda$(dam$^-$) DNA undigested, EcoRI digested, BamHI digested and HindTII digested respectively. The DNA was Southern blotted to a nylon Hybond™ membrane using techniques known to those of skill in the art and UV irradiated for two minutes. Methylated DNA fragments are detected as purple bands on white nylon filter background.

FIG. 7B is a photograph of the nylon membrane after immunochemical detection. It can be seen that SamHI or HindIII digested DNA fragments which were subsequently M.EcoRI (GA$^{6m}$ATTC) methylated can be seen after transfer to nylon membranes and immunochemically detected. These results show that $^{6m}$A sites in DNA which has been enzymatically methylated in vitro can be stained using anti $^{6m}$A antibodies, whereas unmethylated DNA is nonstained. In short, Example 5 shows sequence-specific MTase painting of DNA at 6 bp long GA$^{6m}$ATTC sites.

EXAMPLE 6

Sequence-Specific DNA Methylation and Restriction Digestion Followed by Tm nochemical Detection (DNA Paint)

Figure 8A:
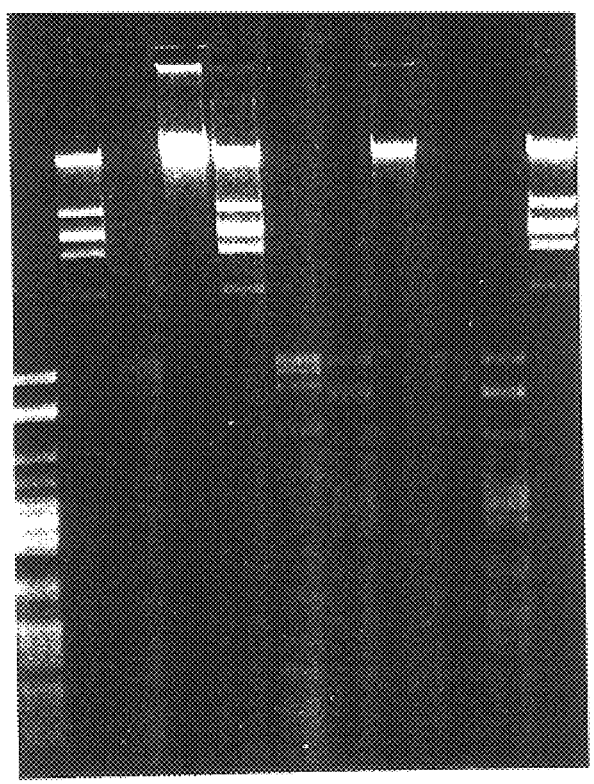
FIGS. 8A and 8B show the immunochemical detection of in vitro methylated DNAs using rabbit anti-6$^m$A antibody and immunoenzymatic staining.

This example is an early sequence specific "purple DNA Paint" experiment showing the specificity of methylation by first methylating with $^{6m}$A$^-$ and $^{5m}$C$^-$ specific methyltransferases, followed by itdmunochemical detection using rabbit anti-$^{6m}$A-antibodies and alkaline phosphatase-conjugated goat anti-rabbit antibodies. (See FIGS. 8A and 8B.)

Methylation was conducted on lambda dam- phage DNA using M.dam MTase (G$^{6m}$ATC, lane D–F), M.EcoRI MTase (G$^{6m}$AATTC, lanes G–I), M.SssI MTase ($^{5m}$CG, lanes J–K), and unmethylated damphage lambda (lanes A–C). The DNA was then digested-with restriction enzymes MboI ($\downarrow$GATC, lanes A, D, G. J), EcoRI (G$\downarrow$AATTC, lanes B, E, H, K) or HpaII (C$\downarrow$CGG, lanes C, F, I) and run out on an agarose gel stained with ethidium bromide (see FIG. 8A). As can be seen in lanes D and H, the digestion is blocked due to the methylation at the sequence-specific restriction site.

Figure 8B:
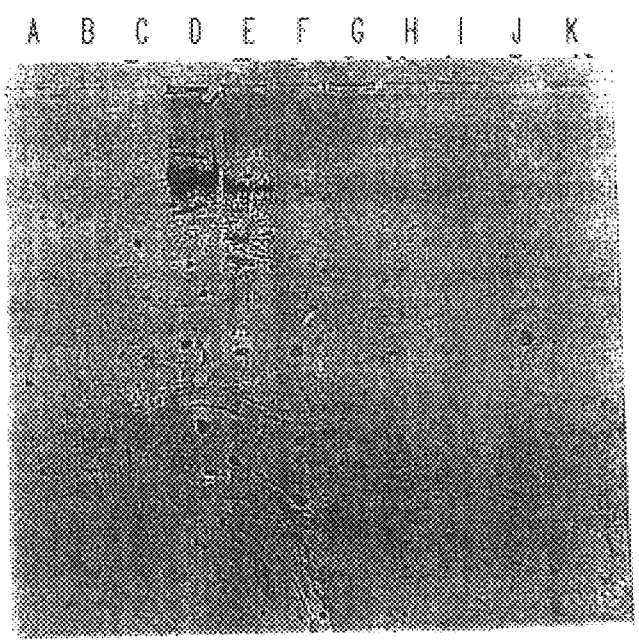

The gel-separated DNA was then transferred to a nylon membrane by Southern blot. The immunochemical detection was performed as described in Example 4. Methylated DNA fragments stain as dark purple bands on a light purple background. Lanes D–I all contain methylated $^{6m}$A sites and Lanes J and K contain methylated $^{5m}$C sites. FIG. 8B is a photograph of the immunostained membrane and shows that only those fragments containing $^{6m}$A-methylated DNA stained purple. While Lanes D–I all contained $^{6m}$A-methylated DNA, only those fragments with at least 6 to 8 $^{6m}$A sites were detected planes D and E).

Figure 9A:
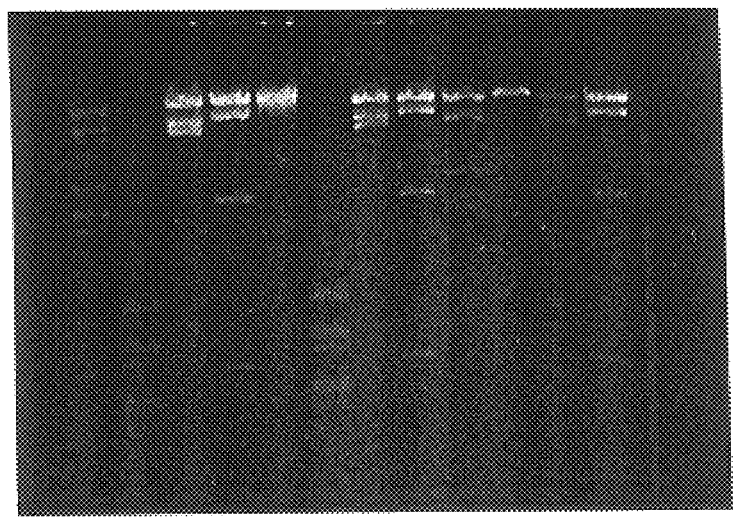
FIGS. 9A and 9B show a sequence-specific "purple DNA Paint" experiment using phage T7 DNA methylated in vitro using M.dam (G$^{6m}$ATC) MTase.
Figure 9B:
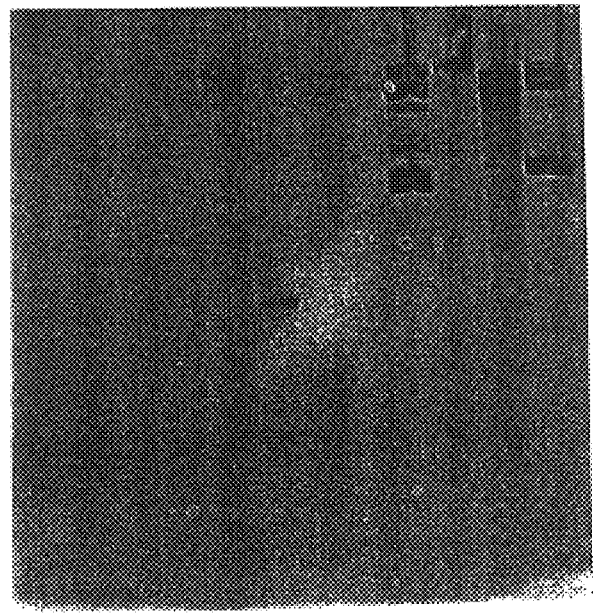

FIGS. 9A and 9B also show a sequence-specific "purple DNA Paint" experiment using phage T7 DNA and M.dam (G$^{6m}$ATC) MTase. DNA was either unmethylated (lanes A, B. C, D) or was G$^{6m}$ATC-methylated with M.dam MTase (lanes E, F, G, H) or TCG$^{6m}$A methylated with M.TaqI MTase (lanes I, J, K, L). The DNAs were then digested using DpnII (IATC) (lanes A, E, I), TaqI (T$\downarrow$CGA) (lanes B, F, J), SpeI (A$\downarrow$CTAGT) (lanes C, G, K), or NruI (TCG$\downarrow$CGA) (lanes D, H, L).

As can be seen in FIG. 9A, lanes A, B, C, D are cut to completion. Lane E shows the G$^{6m}$ATC-methylated DNA did not cut using DpnII($\downarrow$GATC) and lane J shows the TCG$^{6m}$A-methylated DNA did not cut using TaqI(T$\downarrow$CGA). FIG. 9B shows the nylon membrane following transfer of the gel in FIG. 9A.

FIG. 9B is a photograph of the membrane following immunodetection of the $^{6m}$A-methylated DNA. There are no bands in the unmethylated lanes (A, B, C, D). While lanes E through L all show that a sequence-specifically methylated DNA fragment can be detected, lanes I through L appear to give much stronger signal suggesting either a greater number of M.TaqI MTase sites in T7 DNA.

From these figures, the following conclusions can be drawn: (1) It is possible to detect DNA which has been methylated in vitro using Dam (G$^{6m}$ATC) MTase. (2) $^{6m}$A methylated DNA is specifically stained using anti $^{6m}$A antibodies, whereas unmethylated DNA and sUC methylated DNA is unstained.

With modest improvements in sensitivity, it should be possible to detect single MTase sites in restriction fragments from approximately 1–2 $\mu$g of phage $\lambda$ DNA. For example, using more DNA, partially purifying anti-$^{6m}$A IgG's, or sandwich immuno staining protocols (biotinylated goat anti-rabbit antibody and avidin conjugated alkaline phosphatase) should increase sensitivity at least ten-fold.

EXAMPLE 7

Example 7 shows such improved sensitivity. Refinements of our DNA MTase genotyping procedure make it possible to immunochemically "paint" single copy human genes at defined 2 to 6 bp sites using PCR amplification, sequence-specific methylation and immunodetection of $^{6m}$A-labeled DNA. One $^{6m}$A-labeled MTase recognition site in a 536 bp fragment of the single copy human beta globin gene can be detected by improved immunostaining.

Figure 10A:
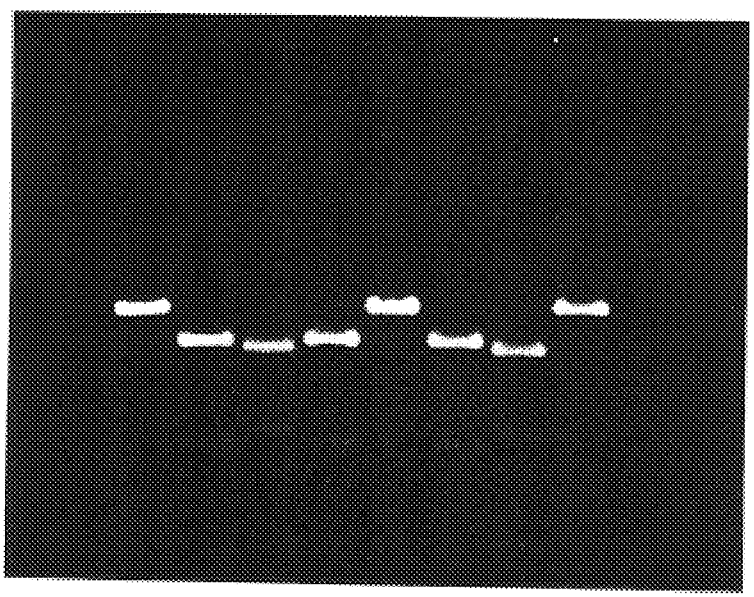
FIGS. 10A, 10B and 10C show a sequence-specific "purple DNA Paint" experiment of an in vitro methylated amplicon from human β-globin gene.
Figure 10B:
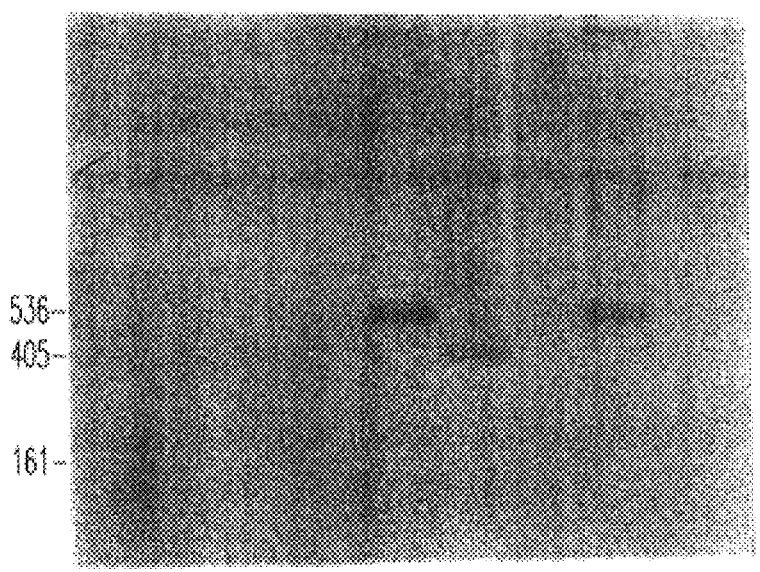
Figure 10C:
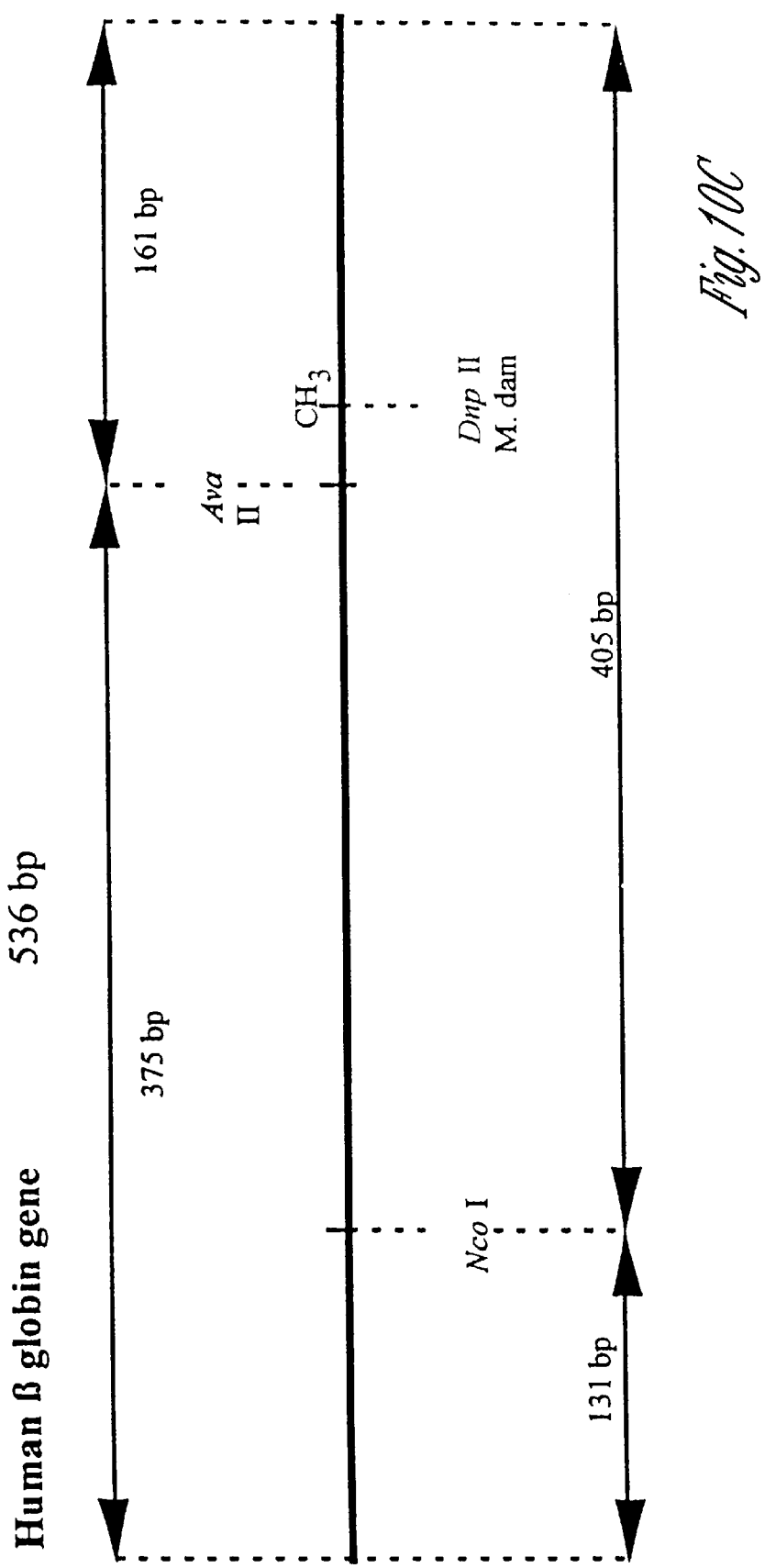

FIGS. 10A, 10B, and 10C show a sequence-specific (purple DNA Paint) experiment of an in vitro methylated amplicon from human $\beta$-globin gene. The 536 bp amplicon is first PCR amplified and then methylated at $G^{6m}ATC$ sites using M.dam MTase. Amplified methylated DNA is then digested with 10 units of restriction endonucleases NcoI (C↓CATGG), AvaII(G↓G(A/T)CC), DpnII(↓GATC) or is left uncut. FIG. 10A shows a 1.7% agarose gel containing the following DNA treatments:

Lane 1; unmethylated, uncut
Lane 2; unmethylated, NcoI
Lane 3; unmethylated, AvaII
Lane 4; unmethylated, DpnII
Lane 5; methylated, uncut
Lane 6; methylated, NcoI
Lane 7; Methylated, AvaII
Lane 8; Methylated, DpnII
Lane 9; BioRad Molecular Weight marker 50–2000 bp.

Note that DpnII(↓GATC) cleavage is completely blocked by M.dam MTase ($G^{6m}ATC$), whereas unmethylated DNA is cut by DpnII.

After 1.7% agarose gel electrophoresis, the gel was Southern blotted to a nylon membrane and uv-crosslinked prior to immunochemical detection (MegaPurple™).

FIG. 10B shows a photograph of the nylon membrane following sequence-specific immunophosphatase/BCIP immunochemical detection of DNA fragments containing $G^{6m}ATC$ sites. By comparing fragment sizes (see map shown in FIG. 10C) with a $G^{6m}ATC$-methylation site it is clear that the 536 and 405 bp fragments are easily detectable. However, the 161 bp fragment of the AvaII digest is barely visible. There is no non-specific background labeling of unmethylated DNA. Therefore, Example 7 demonstrates sequence-specific immunochemical painting of a single methylated $G^{6m}ATC$ site in a 536 bp fragment of a single copy human gene.

EXAMPLE 8

This example demonstrates it is possible to paint methylated DNA fragments larger than 1 kb from a single human gene. Immunochemical detection of in vitro $GA^{6m}ATCC$ methylated PCR amplicon from human β-globin gene after EcoRI, BsrGI or BamHI digestion and Southern blotting to a nylon membrane yields "red DNA Paint" when fast red substrate (Pierce, Rockford, Ill.) is employed for immunostaining.

Figure 11A:
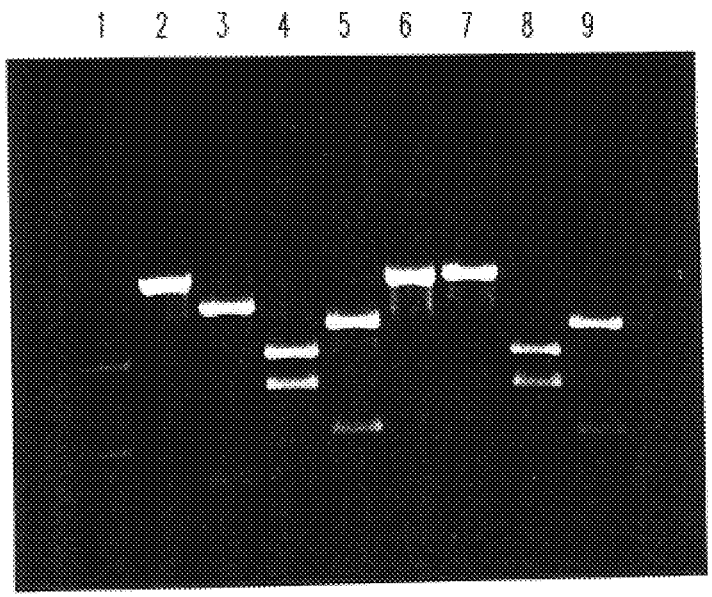
FIGS. 11A, 11B and 11C show a sequence-specific "red DNA Paint" of a 1.85 Kb PCR amplicon from the human β-globin gene. The sensitivity of immunostaining is sufficient to detect a single M.EcoRI MTase site in less than 1 μg of PCR amplified DNA.
Figure 11B:
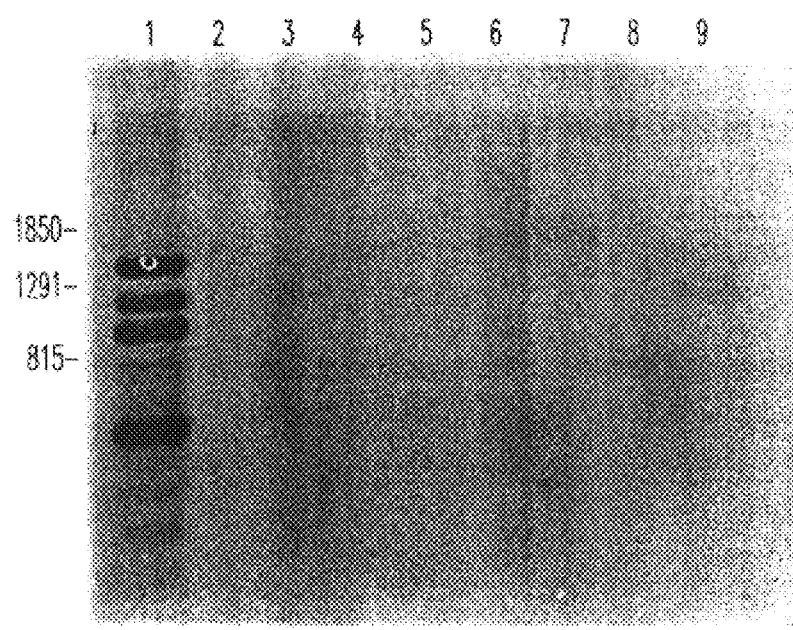
Figure 11C:
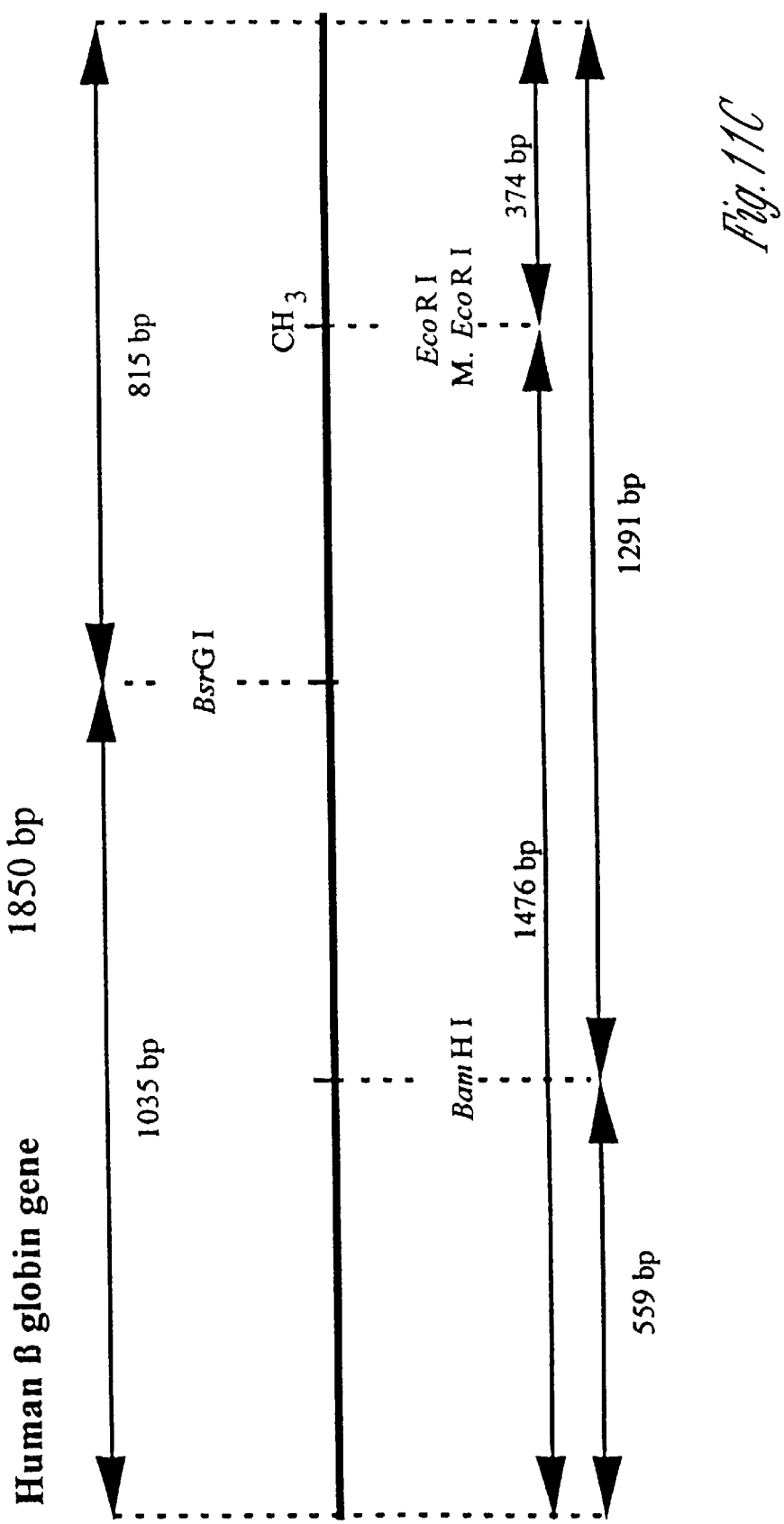

A 1850 bp fragment of untreated or else human β-globin gene is PCR amplified and then either methylated using M.EcoRI MTase ($GA^{6m}ATCC$) or left untreated. Restriction enzyme digests are then conducted on 20 µl aliquot with 10 units of EcoRI (G↓AATTC), BsrGI (T↓GTACA), or BamHI (G↓GATCC) endonuclease. Note that E=RI cleavage is blocked by M.EcoRI MTase methylation; but unmethylated DNA is cut by EcoRI. Methylated or unmethylated DNA restriction fragments are then separated on a 1.7% agarose gel in the following order (see FIG. 11A):

Lane 1; dam+, Molecular Marker, 100 bp DNA Labeling (New England Biolabs)
Lane 2; unmethylated, uncut
Lane 3; unmethylated, EcoRI
Lane 4; unmethylated, BsrGI
Lane 5; unmethylated, BamHI
Lane 6; methylated, uncut
Lane 7; methylated, EcoRI
Lane 8; methylated, BsrGI
Lane 9; methylated, BamHI After 1.7% agarose gel electrophoresis, the gel was Southern blotted to a nylon membrane and uv-crosslinked prior to immunochemical detection (MegaRed™). The immunochemical detection of the $^{6m}A$ methylated DNA using rabbit anti$^{6m}A$ methylated antibodies followed by alkaline-phosphatase anti-rabbit antibodies and fast red substrate is shown in FIG. 11B. Comparison of the "red DNA Paint" results with the map of FIG. 11C shows the fragments containing the $GA^{6m}ATTC$-sequence-specific methylated site were "painted" red by the immunochemical staining method. In other words, DNA fragments as large as 1.8 kb from single copy human genes can be specifically painted at $GA^{6m}ATTC$ sites; and they can be painted red.

EXAMPLE 9

This example shows the precise specificity of the rabbit antibodies, which only recognize 6-methyladenine ($^{6m}A$). DNA which has been enzymatically methylated at $^{4m}C$ or $^{5m}C$ sites is not immunochemically stained. Immunochemical detection of in vitro M.dam methylated PCR amplicon from human β-globin gene after NcoI, DpnII, BstNI or HaeIII digestion and Southern blotting to a nylon membrane selectively identifies those fragments containing $G^{6m}ATC$ sites. Only $^{6m}A$ methylated DNA is "painted red".

A 536 bp fragment of human β-globin gene was PCR amplified using methods described previously. A portion of this amplified DNA was methylated using M. HaeIII MTase ($GGC^{5m}C$), M.dam MTase ($G^{6m}ATC$), or M.MvaI MTase ($C^{4m}CWGG$). Portions of each of these methylated DNAs, as well as unmethylated DNA were then restriction endonuclease digested with 10 units of NcoI(C↓CATGG); DpnII (↓GATC); BstNI(CC↓WGG) or HaeIII (GG↓CC) These DNA samples were then size separated on a 1.7% agarose gel in the following order:

Lane 1; unmethylated; uncut
Lane 2; unmethylated; NcoI
Lane 3; unmethylated; DpnII
Lane 4; unmethylated; BstNI
Lane 5; unmethylated; HaeIII
Lane 6; M. aeIII MTase; uncut
Lane 7; M.HaeII MTase; NcoI
Lane 8; M.HaeII MTase; HaeIII
Lane 9; M.dam MTase; uncut
Lane 10; M.dam MTase; NcoI
Lane 11; M.dam MTase; DpnII
Lane 12; M.MvaI MTase; uncut
Lane 13; M.MaI MTase; NcoI
Lane 14; M.MI MTase; BstNI
Lane 15; Molecular Weight Marker; 50–2000 bp (BioRad)

Figure 12A:
FIGS. 12A, 12B and 12C show a sequence-specific "red DNA Paint" of a PCR amplified product specifically methylated at $^{4m}$C, $^{5m}$C or $^{6m}$A. The sensitivity of the immunostaining is sufficient to detect a single M.EcoRI MTase site (GA$^{6m}$ATTC) in 1 μg of amplified DNA.

Note that kziII cleavage is blocked by M.dam MTase ($G^{6m}ACT$), LIII cleavage is blocked by M. HaeIII MTase ($GGC^{5m}C$), and BstNI cleavage is blocked by M.MvaI MTase ($C^{4m}CWGG$). (See FIG. 12A).

Figure 12B:
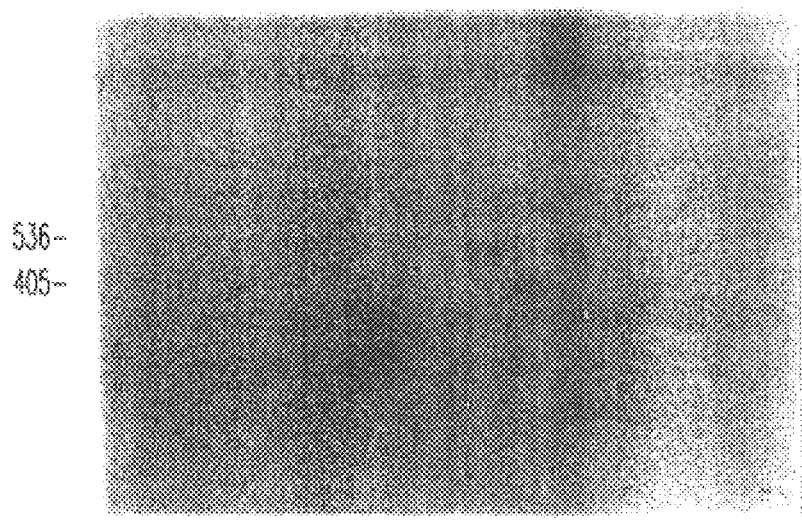
Figure 12C:
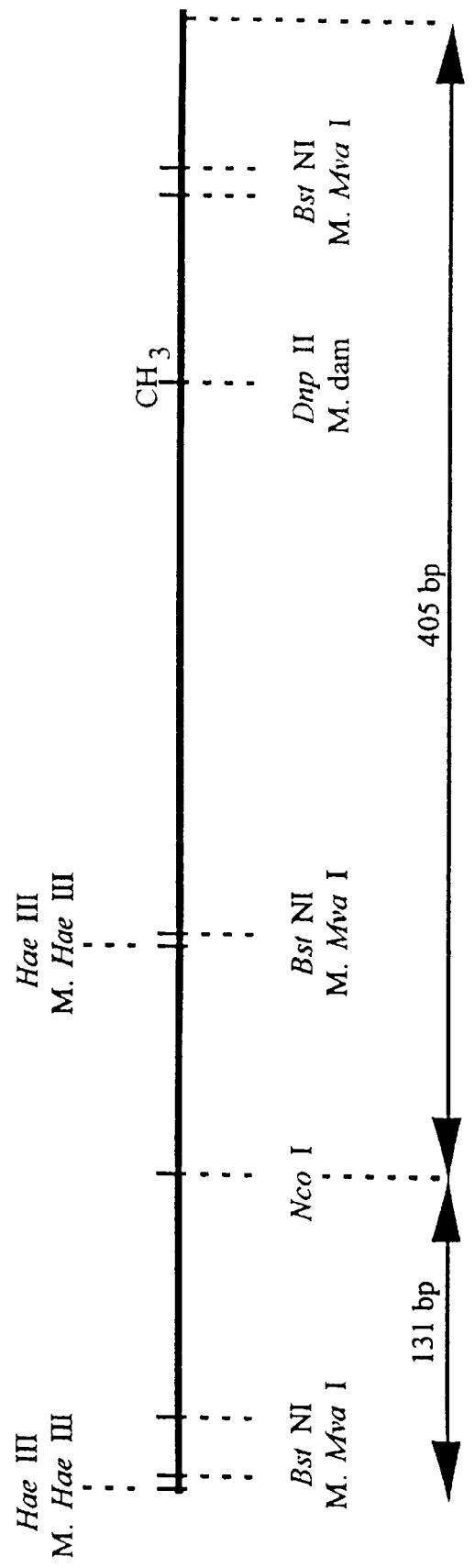

After 1.7% agarose gel electrophoresis, the gel was Southern blotted to a nylon membrane and uv-crosslinked prior to immunochemical detection (MegaRed™) (See FIG. 12B) FIG. 12C shows a map of the β-globin 536 bp amplicon exhibiting the expected sizes of methylated DNA fragments. By comparing FIG. 12B and FIG. 12C it is clear that all unmethylated lanes (1–5 and 15) are not labeled by "red DNA Paint" specific for $^{6m}A$ methylated DNA. Further, the $^{5m}C$ methylated DNA lanes (6–8) and the $^{4m}C$ methylated DNA lanes (12–14) are also not "painted red".

However, the 536 bp DNA amplicon of M.dam MTase methylated DNA of lane 9, the 405 bp fragment of NcoI digested M.dam MTase methylated DNA of lane 10, and the uncut 536 mp DNA amplicon of DpnII digested M.dam MTase methylated DNA of lane 11 are all painted red by the "red DNA Paint" reaction of the present invention. In this example, the immunochemical detection of the $^{6m}$A methylated DNA is accomplished using rabbit anti-$^{6m}$A IgG antibody followed by alkaline phosphatase anti-rabbit IgG and Fast Red™ substrate (Pierce, Rockford, Ill.).

In short, Example 9 shows that DNA which is unmethylated, $^{4m}$C-methylated, or $^{5m}$C-methylated is not stained by anti $^{6m}$A antibody. In contrast, DNA which has been methylated at G$^{6m}$ATC sites in vitro by M.dam MTase is immunostained red.

What is claimed is:

1. A method for identifying DNA genotype comprising:
   methylating DNA utilizing a DNA methyltransferase specific for a sequence recognition site, wherein the recognition site is about 2 to about 8 base pairs;
   assaying for the presence of the methylation at the sequence recognition site; and
   determining the allele composition at the sequence recognition site.

2. The method of claim 1 wherein the means of assaying for the presence of methylation is immunochemical or radiometric.

3. The method of claim 1 wherein the radioactively-labeled methyl-SAM is $^3$H-methyl-SAM.

4. A method for identifying a DNA genotype comprising:
   amplifying a DNA fragment using a Polymerase and primers flanking a DNA methyltransferase recognition sequence wherein an allele contains the recognition sequence and another allele does not contain the recognition sequence;
   methylating the DNA fragment utilizing a DNA methyltransferase that recognizes the recognition site and radioactively-labeled-methyl-SAM in appropriate methylation buffer;
   assaying for the presence of radioactively-labeled-methylated DNA, wherein the recognition site is about 2 to about 8 base pairs; and
   determining allele composition at the recognition sequence site.

5. The method of claim 4 wherein the primers are selected to create an amplified DNA fragment capable of identifying a DNA genotype.

6. The method of claim 4 wherein the primers are selected to create an amplified DNA fragment in the range of about 30–100 base pairs.

7. The method of claim 4 wherein the DNA genotype is determined qualitatively as a positive for homozygous alleles a or heterozygous for alleles a/b and negative for alleles b/b.

8. The method of claim 4 wherein the DNA genotype is determined quantitatively as a range of counts per minute for alleles a/a, a/b and b/b.

9. The method of claim 4 wherein the DNA fragment is amplified using polymerase chain reaction technique.

10. The method of claim 4 wherein the DNA fragment is amplified using strand displacement amplification.

11. The method of claim 4 wherein one of the primers is biotinylated.

12. The method of claim 11 wherein the resulting DNA fragment is captured on a streptavidin-coated fluoromicrosphere.

13. A method for identifying a DNA genotype comprising:
    amplifying and methylating a DNA fragment in a single reaction mixture using an appropriate buffer solution and a thermostable DNA methyltransferase, radioactively-labeled-methyl-SAM, polymerase and primers flanking the thermostable DNA methyltransferase recognition sequence wherein an allele contains the recognition sequence and another allele does not contain the recognition sequence;
    assaying for the presence of radioactively-labeled-methylated DNA; and
    determining allele composition at the recognition sequence site.

14. The method of claim 13 wherein the radioactively-labeled-methyl-SAM is $^3$H-methyl-SAM.

15. The method of claim 13 wherein the primers are selected to create an amplified DNA fragment capable of identifying a DNA genotype.

16. The method of claim 13 wherein the primers are selected to create an amplified DNA fragment in the range of about 30–70 base pairs.

17. The method of claim 13 wherein the DNA genotype is determined qualitatively as a positive for homozygous alleles a or heterozygous for alleles a/b and negative for alleles b/b.

18. The method of claim 13 wherein the DNA genotype is determined quantitatively as a range of counts per minute for alleles a/a, a/b and b/b.

19. The method of claim 13 wherein the DNA fragment is amplified using polymerase chain reaction technique.

20. The method of claim 13 wherein the DNA fragment is amplified using strand displacement amplification.

21. The method of claim 13 wherein one of the primers is biotinylated.

22. The method of claim 21 wherein the resulting DNA fragment is captured on a streptavidin-coated fluoromicrosphere.

23. A method for genotyping DNA comprising:
digesting the DNA with a restriction endonuclease;
methylating the DNA utilizing radioactively-labeled-methyl-SAM and a DNA methyltransferase specific for a recognition sequence different than the recognition sequence of the restriction endonuclease;
separating the digested, methylated DNA on an agarose gel;
transferring the separated, digested, methylated DNA onto a membrane; and
identifying a banding pattern specific for the restriction endonuclease/DNA methyltransferase/DNA utilizing a radiometric assay
wherein the presence or absence of methylated from 2 to about 8 base pairs DNA Mtase recognition sites appear as the banding pattern.

24. The method of claim 23 wherein the radioactively-labeled-methyl-SAM is $^3$H-methyl-SAM.

25. A method for genotyping DNA comprising:
digesting the DNA with a restriction endonuclease;
methylating the DNA utilizing methyl-SAM and a DNA methyltransferase specific for a recognition sequence different than the recognition sequence of the restriction endonuclease;
separating the digested, methylated DNA on an agarose gel;
transferring the separated, digested, methylated DNA onto a membrane; and
identifying a banding pattern specific for the restriction endonuclease/DNA methyltransferase/DNA utilizing an immunochemical technique
wherein the presence or absence of methylated from 2 to about 8 base pairs DNA Mtase recognition sites appear as the banding pattern.

26. The method of claim 25 wherein the immunochemical technique utilizes an antibody to the methylated DNA and a secondary antibody to the antibody to the methylated DNA conjugated to an enzymatic staining element whereby a substrate is then added to the antibody-secondary antibody-enzyme conjugate to form a detectable color.

27. The method of claim 26 wherein the antibody is rabbit anti-$^{6m}$A antisera.

28. The method of claim 26 wherein the secondary antibody is alkaline-phosphatase conjugated goat anti-rabbit antibody.

29. The method of claim 26 wherein the antibody is rabbit anti-$^{5m}$C antisera.

30. The method of claim 26 wherein the antibody is a monoclonal antibody selected from the group consisting of anti-$^{6m}$A antibody, anti-$^{5m}$C antibody, and anti-$^{4m}$C antibody.

31. The method of claim 26 wherein the secondary antibody is horseradish-peroxidase-conjugated goat anti-rabbit antibody.

32. A method for identifying a DNA genotype comprising:
amplifying a DNA fragment using a Polymerase and primers flanking a DNA methyltransferase recognition sequence wherein an allele contains the recognition sequence and another allele does not contain the recognition sequence;
methylating the DNA utilizing a DNA methyltransferase that recognizes from about 2 to about 8 base pair sequence recognition sites and methyl-SAM in an appropriate methylation buffer;
removing unincorporated methyl-groups;
dotting dilutions of DNA onto membrane; and
determining allele composition utilizing an immunochemical technique.

33. The method of claim 32 wherein the immunochemical technique utilizes an antibody to the methylated DNA and a secondary antibody to the antibody to the methylated DNA conjugated to an enzymatic staining element whereby a substrate is then added to the antibody-secondary antibody-enzyme conjugate to form a detectable color.

34. The method of claim 33 wherein the antibody is rabbit anti-$^{6m}$A antisera.

35. The method of claim 33 wherein the secondary antibody is alkaline-phosphatase conjugated goat anti-rabbit antibody.

36. The method of claim 33 wherein the antibody is rabbit anti-$^{5m}$C antisera.

37. The method of claim 33 wherein the secondary antibody is horseradish-peroxidase-conjugated goat anti-rabbit antibody.

38. The method of claim 32 wherein the primers are selected to create an amplified DNA fragment less than or equal to about 200 base pairs.

39. The method of claim 32 wherein the primers are selected to create an amplified DNA fragment in the range of about 30–100 base pairs.

40. The method of claim 32 wherein the DNA genotype is determined qualitatively as a positive for homozygous alleles a or heterozygous for alleles a/b and negative for alleles b/b.

41. The method of claim 40 wherein the DNA genotype is determined utilizing binary code.

42. The method of claim 32 wherein the DNA genotype is determined quantitatively as a range of detectable color for alleles a/a, a/b and b/b.

43. The method of claim 41 wherein the DNA genotype is determined utilizing ternary code.

44. The method of claim 32 wherein the DNA fragment is amplified using polymerase chain reaction technique.

45. The method of claim 32 wherein the DNA fragment is amplified using strand displacement amplification.

46. A method for generating ordered maps from a DNA fragment comprising:
amplifying a DNA fragment using a Polymerase and primers flanking a region of DNA to be mapped wherein one of the primers is biotinylated;
digesting the DNA fragments with a series of specific restriction endonucleases;
methylating each restriction endonuclease digested DNA fragment utilizing $^3$H-methyl-SAM and a series DNA methyltransferases wherein one of the DNA methyltransferases recognizes the same recognition sequence as the restriction endonuclease and the other DNA methyltransferases recognize different recognition sequences than the restriction endonuclease;

anchoring each amplicon to a streptavidin-coated magnetic bead via the biotin present in the biotinylated primer;

removing unanchored DNA;

treating the bead-anchored DNA with Proteinase K to remove DNA from bead;

removing the bead;

assaying for the presence of $^3$H-methylated DNA; and creating an ordered map based on presence or absence of the $^3$H-methylated DNA.

47. The method of claim 46 wherein the DNA fragment is amplified using polymerase chain reaction technique.

48. The method of claim 46 wherein the DNA fragment is amplified using strand displacement amplification.

* * * * *

SEQUENCE LISTING

<160> NUMBER OF SEQ ID NOS: 8

<210> SEQ ID NO 1
<211> LENGTH: 362
<212> TYPE: DNA
<213> ORGANISM: Homo sapiens

<400> SEQUENCE: 1
ggtgggagaa gaagataaaa agtaacatct ttctgccttc cagatgattc gaagaatttc      60
tccatccaag tgcggcaggt ggaggattgc cctgtggaca tctactactt gatggacctg     120
tcttactcca tgccggatga tctgtggagc atccagaacc tgggtaccaa gctggccacc     180
cagatgcgaa agctcaccag taacctgcgg attggcttcg gggcatttgt ggacaagcct     240
gtgtcaccat acatgtatat ctccccacca gaggccctcg aaaaccctg ctatgagtaa     300 gtccctcctc cagacgccag gacagcatcc tttgcccagg aaggtccaag tcctggttcc     360
ta                                                                   362

<210> SEQ ID NO 2
<211> LENGTH: 61
<212> TYPE: DNA
<213> ORGANISM: Homo sapiens

<400> SEQUENCE: 2
gaacctgggt accaagcttg gccacccaga tgcgaagctc accagtaacc tgcggattgg      60
c                                                                    61

<210> SEQ ID NO 3
<211> LENGTH: 22
<212> TYPE: DNA
<213> ORGANISM: Homo sapiens

<400> SEQUENCE: 3
ggtgggagaa gaagataaaa ag                                              22

<210> SEQ ID NO 4
<211> LENGTH: 20
<212> TYPE: DNA
<213> ORGANISM: Homo sapiens

<400> SEQUENCE: 4
ccaggttcag gaccaaggat                                                 20

<210> SEQ ID NO 5
<211> LENGTH: 103
<212> TYPE: DNA
<213> ORGANISM: Herpes simplex virus 1

<400> SEQUENCE: 5
ccaagctgac ggacatctac aaggtccccc tggacgggta cggccgcatg aacggccggg      60

-continued

```
gcgtgtttcg cgtgtgggac ataggccaga gccacttcca gaa        103

<210> SEQ ID NO 6
<211> LENGTH: 103
<212> TYPE: DNA
<213> ORGANISM: Herpes simplex virus 2

<400> SEQUENCE: 6
ccaagctgac ggagatctac aaggtcccgc tcgacgggta cgggcgcatg aacggccggg    60
gtgtgttccg cgtgtgggac atcggccaga gccacttcca gaa        103

<210> SEQ ID NO 7
<211> LENGTH: 22
<212> TYPE: DNA
<213> ORGANISM: Homo sapiens

<400> SEQUENCE: 7
gaacctgggt accaagcttc gc                               22

<210> SEQ ID NO 8
<211> LENGTH: 22
<212> TYPE: DNA
<213> ORGANISM: Homo sapiens

<400> SEQUENCE: 8
gtggtcattg gactcctaac cg                               22
```